US008703723B2

(12) United States Patent
Hutchinson et al.

(10) Patent No.: US 8,703,723 B2
(45) Date of Patent: *Apr. 22, 2014

(54) GLYCOSIDE COMPOUNDS AND PHARMACEUTICAL COMPOSITIONS THEREOF

(71) Applicant: Jill Hutchinson-Bollettieri, St. Louis Park, MN (US)

(72) Inventors: Charles R. Hutchinson, Madison, WI (US); Mohammed S. Shekhani, Madison, WI (US); James R. Prudent, Madison, WI (US)

(73) Assignee: Centrose, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/728,639

(22) Filed: Dec. 27, 2012

(65) Prior Publication Data

US 2013/0178431 A1 Jul. 11, 2013

Related U.S. Application Data

(63) Continuation of application No. 13/057,961, filed as application No. PCT/US2009/053159 on Aug. 7, 2009, now Pat. No. 8,361,973.

(51) Int. Cl.
*A01N 45/00* (2006.01)
*C07J 41/00* (2006.01)
*C07G 3/00* (2006.01)

(52) U.S. Cl.
USPC ..................... 514/26; 536/5; 536/6

(58) Field of Classification Search
None
See application file for complete search history.

(56) References Cited

U.S. PATENT DOCUMENTS

| | | | | |
|---|---|---|---|---|
| 3,915,957 | A | * | 10/1975 | Kaiser et al. ............ 536/6.1 |
| 3,987,031 | A | | 10/1976 | Losel et al. |
| 4,555,504 | A | * | 11/1985 | Jones ........................ 514/26 |
| 5,280,113 | A | | 1/1994 | Rademacher et al. |
| 5,668,272 | A | | 9/1997 | Prasad et al. |
| 6,180,612 | B1 | * | 1/2001 | Hockensmith et al. ....... 514/25 |
| 7,754,874 | B2 | | 7/2010 | Thorson et al. |
| 8,187,644 | B2 | | 5/2012 | Addington |
| 2006/0041109 | A1 | | 2/2006 | Thorson et al. |
| 2007/0172422 | A1 | | 7/2007 | Glazier |
| 2008/0003230 | A1 | | 1/2008 | Adair |
| 2009/0202536 | A1 | | 8/2009 | Ebens, Jr. et al. |

FOREIGN PATENT DOCUMENTS

| | | |
|---|---|---|
| WO | WO-2007081835 A2 | 7/2007 |
| WO | WO-2008121797 A1 | 10/2008 |
| WO | WO-2010017480 A1 | 2/2010 |

OTHER PUBLICATIONS

Takechi et al., Phytochemistry, vol. 41(1), 1996, pp. 125-127.*
Schoenfeld et al., AN1989:108333—Quantitative Structure-Activity relationships, 7(3), 1988.*
Caldwell et al., The Journal of Pharmacology and Experimental Therapeutics, vol. 197(1), Apr. 1976, pp. 19-26.*
Banker, G.S. et al., "Modern Pharmaceutics, 3ed.", Marcel Dekker, New York, 1996, p. 596.
International Preliminary Report on Patentability for corresponding PCT Application No. PCT/US09/53159 (Feb. 8, 2011).
International Search Report for corresponding PCT Application No. PCT/US09/53159 (Sep. 21, 2009).
International Search Report for International Application No. PCT/US2010/048284, dated Dec. 20, 2010.
Khan, M.S.Y. et al., "A comprehensive review on the chemistry and pharmacology of *Corchorus* species—A source of cardiac glycosides, triterpenoids, ionides, flavinoids, coumarins, steroids and some other compounds," Journal of Scientific & IndustrialResearch, Apr. 2006, vol. 65, pp. 283-298.
Langenhan et al., "Enhancing The Anticancer Properties of Cardiac Glycosides by Neoglycorandomization," Proceedings of The National Academy of Sciences, National Academy of Sciences, US, vol. 102, No. 35, Jan. 1, 2005, pp. 12305-12310.
Supplemental European Search Report for European Application No. 09805612; Date of Mailing: Feb. 27, 2013; 16 pages.
Takechi, et al., "Structure-Activity Relationships of Synthetic Digitoxigenyl Glycosides," Phytochemistry, vol. 37, No. 5, pp. 1421-1423, 1994.
Wolff, Manfred E. "Burger's Medicinal Chemistry, 5ed, Part 1", John Wiley & Sons, 1995, pp. 975-977.

* cited by examiner

*Primary Examiner* — Traviss C McIntosh, III
(74) *Attorney, Agent, or Firm* — Perkins Coie LLP

(57) ABSTRACT

The present invention provides glycoside compounds, methods of preparing such compounds, pharmaceutical compositions comprising such compounds, and a method for the treatment of hyperproliferative diseases using the same.

6 Claims, 4 Drawing Sheets

GLYCOSIDE COMPOUNDS AND PHARMACEUTICAL COMPOSITIONS THEREOF

PRIORITY CLAIM

This application is a continuation of U.S. patent application Ser. No. 13/057,961, filed on Apr. 8, 2011, now U.S. Pat. No. 8,361,973, which is a national stage application of International Application No. PCT/US2009/017480, filed on Aug. 7, 2009, which claims priority to U.S. Provisional Patent Application Ser. No. 61/087,010, filed on Aug. 7, 2008, the entire contents of each of which are hereby incorporated by reference.

BACKGROUND

Cardiac glycosides have been recognized as potential cancer drugs at least since 1999 (Haux, *Med Hypotheses.* 53:543-8, 1999) and extensive studies of their cytotoxicity in human cancer cells were carried out as early as 2001 (Johansson, et al., *Anticancer Drugs.* 12:475-83, 2001). Interest in the mechanism of inhibition of the cardiac glycosides' target, the inotropic Na,K-ATPases found in the membranes of animal cells, has spawned a considerable body of work (Mijatovic, et al., *Biochim Biophys Acta.* 1776:32-57, 2007). Extensive medicinal chemistry research directed at finding more potent and less toxic cardiac glycosides through chemical modification of their steroid and sugar portions has also been conducted (Repke, K. R., et al., *Progress in Medicinal Chemistry.* 30:135-202, 1993; Mudge, et al., *Circ Res.* 43:847-54, 1978; Repke, K. R. H., Drug Discovery Today. 2:110-16, 1997). Yet despite the synthesis of many different analogs (Repke, K. R., et al., *Progress in Medicinal Chemistry.* 30:135-202, 1993; Schneider and Wolfling, *Curr Org Chem.* 8:1381-403, 2004), some of which include the synthesis of specific cardiac glycosides as cancer drugs, exemplified by the work on digitoxin neoglycoside analogs (Langenhan, et al., *Proc Natl Acad Sci USA.* 102:12305-10, 2005) and on proscillaridin analogs (Gardiner, et al., *USPTO.* A1:1-67, 2009), few cardiac glycosides are currently undergoing clinical development—perhaps due to the widespread belief that cardiac glycosides cannot be used for cancer therapeutically without significant toxicity to heart and neural tissues.

SUMMARY OF THE INVENTION

In one aspect, the present invention provides novel glycoside compounds of the structure of Formula (I) and Formula (II) below. In various embodiments, these compounds are selected from the group consisting of CEN08-177, CEN08-178, CEN08-193, CEN08-243 and CEN08-244. In another aspect, the present invention provides methods of making the compounds as described herein and particularly compounds of Formula (I) and (II). In another aspect, the invention provides pharmaceutical compositions comprising such compounds and at least one pharmaceutically acceptable excipient. In yet another aspect, the invention provides a method of treating a hyperproliferative disease by administering a therapeutically effective amount of a compound or pharmaceutical composition as described herein to a subject in need thereof.

In one embodiment, the invention provides a method of treating cancer in a subject in need thereof comprising administering a therapeutically effective amount of a glycoside compound (or pharmaceutical composition comprising the same) as set forth herein to a subject in need of such treatment. In another embodiment, the glycoside is of Formula (I) below. In still another embodiment, the glycoside compound is of Formula (II) below. In further embodiments, the glycoside is selected from the group consisting of CEN08-177, CEN08-178, CEN08-193, CEN08-243, CEN08-244, and combinations thereof.

In further embodiments, the present invention provides methods for preparing glycosides of Formula (I) and Formula (II). In one embodiment, the glycoside is selected from the group consisting of CEN08-177, CEN08-178, CEN08-193, CEN08-243, CEN08-244.

These and other embodiments of the present invention are described in further detail herein below.

DETAILED DESCRIPTION

Figure 1:
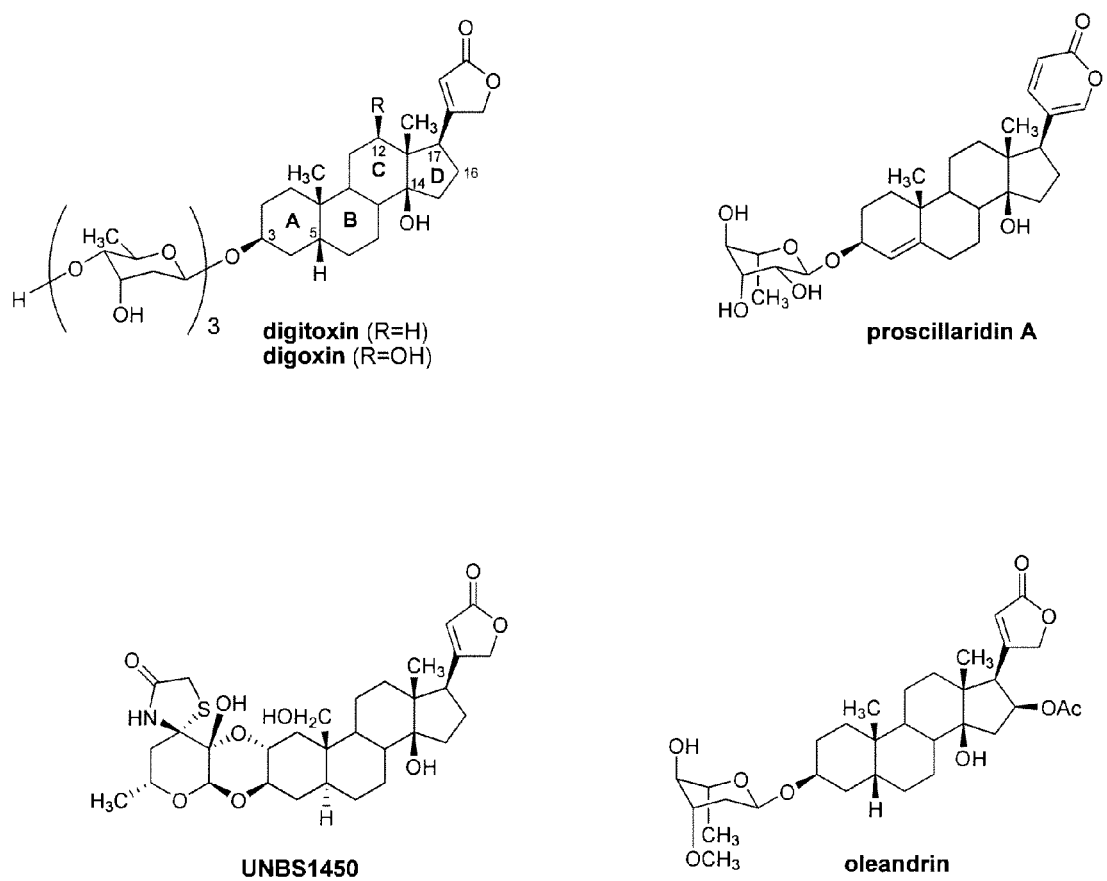
FIG. 1 shows various cardiac glycoside structures, including the structures of cardiac glycosides currently in clinical trials.

While the present invention is capable of being embodied in various forms, the description below of several embodiments is made to exemplify the invention and not to limit the invention to the specific embodiments described. Headings are provided for convenience only and are not to be construed to limit the invention. Embodiments illustrated under any heading may be combined with embodiments illustrated under any other heading.

The use of numerical values in the various quantitative values specified herein are, unless expressly indicated otherwise, stated as approximations and should be read as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein, and in all instances such ratios, ranges, and ranges of ratios represent various embodiments of the present invention.

In one aspect, the invention provides glycoside compounds of Formula (I) as well as pharmaceutically acceptable esters, derivatives, conjugates, hydrates, solvates, prodrugs and salts thereof, or mixtures of any of the foregoing:

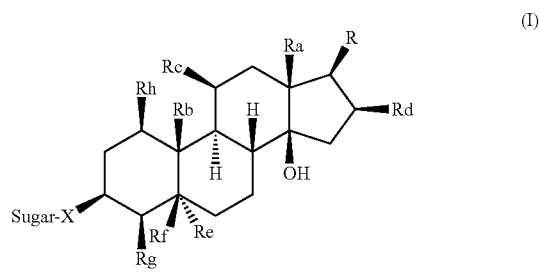

(I)

where the steroidal rings are either saturated, unsaturated or a combination thereof,

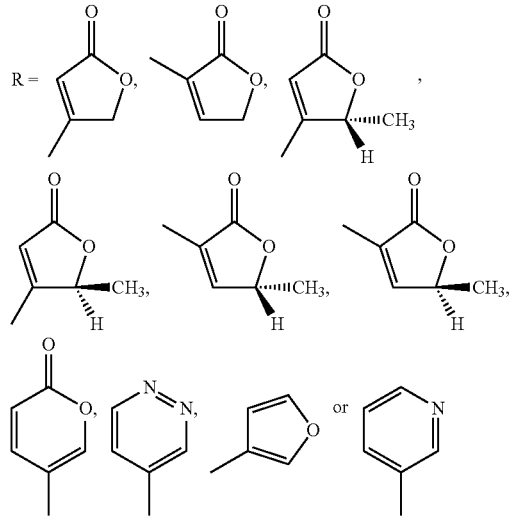

$R^a$ is $CH_3$;

$R^b$ is $CH_3$, $CH_2OH$, or $CHO$;

$R_c$ is H, OH or $CH_3COO$;

$R_d$ is H, OH or $CH_3COO$;

$R_e$ is H or no group;

$R_f$ is H, OH or, when $R_e$ is H or a C=C exists between the atoms joined to $R_e$, $R_f$ and $R_g$, $R_f$ is no group;

$R_g$ is H or, when $R_e$ is H or a C=C exists between the atoms joined to $R_e$, $R_f$ and $R_g$, $R_g$ is no group;

$R_h$ is H or OH;

X is O or N(OR');

R' is an alkyl or aryl group; and

Sugar is D or L of hexose, pentose, deoxyhexose, deoxypentose, deoxy-halohexose, deoxy-halopentose, deoxy-aminopentose, deoxy-aminohexose, tetrose, heterosugar, carboxysugar, a derivative of the aforementioned sugars, a disaccharide derived from at least one of the aforementioned sugars, or a polysaccharide derived from at least one of the aforementioned sugars. Suitable sugars include, e.g., L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, D-glucose, and mixtures thereof.

In another embodiment, the invention provides glycoside compounds of Formula (II) as well as pharmaceutically acceptable esters, derivatives, conjugates, hydrates, prodrugs, solvates and salts thereof, and mixtures of any of the foregoing:

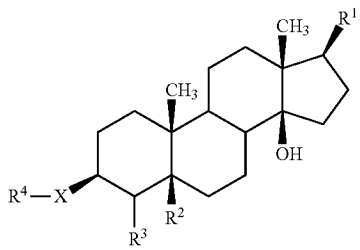
(II)

wherein $R^1$ is selected from the group consisting of

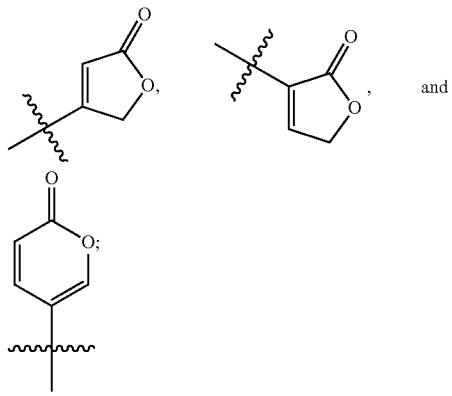
and $R^2$ and $R^3$ are each independently hydrogen, or $R^2$ and $R^3$ along with the attached carbons represent a carbon-carbon double bond;

$R^4$ is selected from the group consisting of

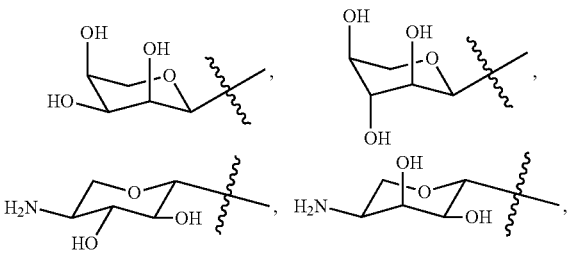

and their epimers and conformers; and X is O or $NR^5$, wherein $R^5$ is selected from hydrogen, methyl, ethyl, isopropyl and propyl.

In still other embodiments, the invention provides compounds of Formula (II) wherein when X=NMe, $R^1$ is

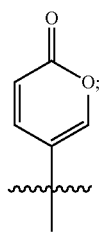 [SMILES: *c1ccc(=O)oc1]

$R^2$ and $R^3$ together with the attached carbons represent a carbon-carbon double bond; and $R^4$ is selected from the group consisting of

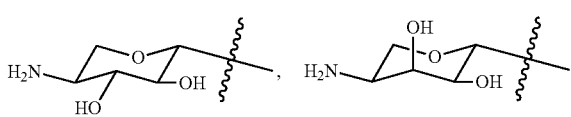 [SMILES: *C1OCC(N)C(O)C1O ; *C1OCC(N)C(O)C1O]

and their epimers and conformers.

In other embodiments, compounds of formula II are provided wherein when X=O, $R^1$ is selected from the group consisting of

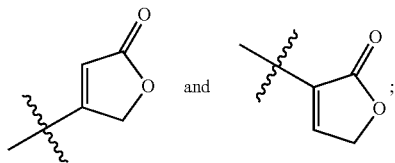 [SMILES: *C1=CC(=O)OC1 ; *C1=CCOC1=O]

$R^2$ and $R^3$ are each hydrogen, and $R^4$ is selected from the group consisting of

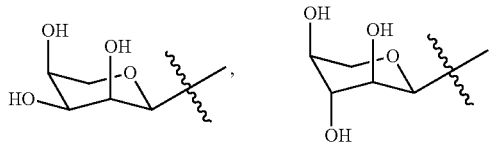 [SMILES: *C1OCC(O)C(O)C1O ; *C1OCC(O)C(O)C1O]

and their epimers and conformers.

In another embodiment, the invention provides a compound of Formula (II) wherein X=O; $R^1$ is

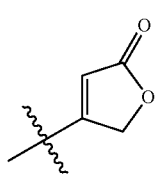 [SMILES: *C1=CC(=O)OC1]

and $R^4$ is

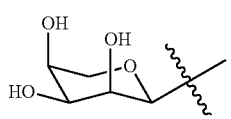

and its epimers and conformers.

In still another embodiment, the invention provides a glycoside compound of Formula (II) wherein X=O; $R^1$ is

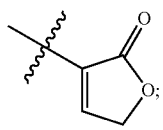 [SMILES: *C1=CCOC1=O]

and $R^4$ is selected from

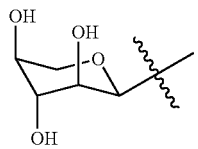 [SMILES: *C1OCC(O)C(O)C1O]

and its epimers and conformers.

In yet another embodiment, the invention provides a glycoside compound of Formula (II) wherein X=NMe; $R^1$ is

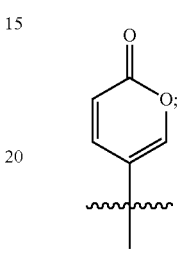

$R^2$ and $R^3$ along with the attached carbons represent a carbon-carbon double bond; and R4 is selected from

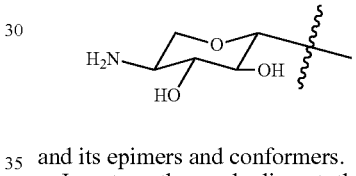

and its epimers and conformers.

In yet another embodiment, the invention provides a glycoside compound of Formula (II) wherein X=NMe; $R^1$ is

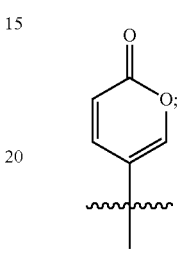

$R^2$ and $R^3$ along with the attached carbons represent a carbon-carbon double bond; and R4 is selected from

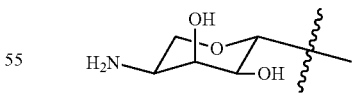

and its epimers and conformers.

In one embodiment, the glycoside compound comprises CEN08-178 (3-O-digitoxigenin-L-riboside), CEN08-193 (3-O-isodigitoxigenin-L-xyloside), CEN08-243 ((3S)-3-N-methoxyamino-scillarenin-L-neo-4-amino-4-deoxyxyloside), or CEN08-244 ((3S)-3-N-methoxyamino-scillarenin-L-neo-4-amino-4-deoxyriboside).

Processes for synthesizing any of the foregoing compounds represent further embodiments of the present invention.

Pharmaceutical Compositions

In another aspect, the invention provides a pharmaceutical composition comprising one or more glycoside compounds of Formula (I) or (II) and at least one pharmaceutically acceptable excipient. In one embodiment, the composition is formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (e.g. 2, 3, 4 or 5) of times per day, or as many times as needed to elicit a therapeutic response.

In one embodiment, a dosage unit as disclosed herein comprises a glycoside compound of Formula (I) or (II) in an amount of about 0.1 mg to about 1 g, about 0.5 mg to about 750 mg, or about 1 mg to about 500 mg, for example about 0.1 mg, about 0.5 mg, about 1 mg, about 5 mg, about 10 mg, about 50 mg, about 100 mg, about 150 mg, about 250 mg, about 300 mg, about 400 mg, about 500 mg, about 600 mg or about 700 mg.

In another embodiment, compositions of the invention are deliverable intravenously and orally. The terms "orally deliverable" or "oral administration" herein include any form of delivery of a therapeutic agent or a composition thereof to a subject wherein the agent or composition is placed in or passes through the mouth of the subject, whether or not the agent or composition is swallowed. Thus "oral administration" includes buccal and sublingual as well as esophageal and pulmonary administration. In other embodiments, compositions of the invention can be administered rectally, parenterally, (for example, intramuscularly, or subcutaneously) intracisternally, intraperitoneally, locally (for example, powders, ointments or drops), topically, or intranasally.

In some embodiments, compositions of the invention are in the form of solid dosage forms. Non-limiting examples of suitable solid dosage forms include tablets (e.g. suspension tablets, bite suspension tablets, rapid dispersion tablets, chewable tablets, melt tablets, effervescent tablets, bilayer tablets, etc), caplets, capsules (e.g. a soft or a hard gelatin capsule filled with solid and/or liquids), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

In other embodiments, compositions of the invention are in the form of liquid or semi-solid dosage forms or units. Non-limiting examples of suitable liquid/semi-solid dosage forms include solutions, suspension, elixirs, syrups, liquid aerosol formulations, liniments, lotions, oil-in-water or water-in-oil emulsions such as creams, ointments or pastes, etc.

In one embodiment, a liquid composition comprising water can be prepared. In another embodiment, compositions of the invention are in the form of a powder for suspension or injection that can be dispersed, suspended or dissolved in a liquid vehicle prior to administration to a subject. While the powder for reconstitution itself can be a solid dosage form of the present invention, the powder dispersed, suspended or dissolved in liquid also comprises a liquid embodiment of the invention.

Pharmaceutical compositions of the invention optionally comprise one or more pharmaceutically acceptable excipients. The term "pharmaceutically acceptable excipient" refers to any substance, not itself a therapeutic agent, used as a carrier or vehicle for delivery of a therapeutic agent to a subject or added to a pharmaceutical composition to improve its handling or storage properties or to permit or facilitate formation of a dosage unit of the composition, and that does not produce unacceptable toxicity or interaction with other components in the composition.

In one embodiment, compositions of the invention comprise at least one pharmaceutically acceptable solvent, co-solvent, and/or solubilizing agent (collectively referred to herein as solubilizers). Non-limiting examples of suitable solubilizers include polyethylene glycol (PEG), ethanol, dimethylacetamide (DMAC), propylene glycol, cyclodextrins, and mixtures thereof.

Cyclodextrins suitable for use in a composition of the invention can be α-cyclodextrins or β-cyclodextrins (also referred to herein as β-CD).

In one embodiment, the cyclodextrin is a partially etherified β-cyclodextrin, substantially as is described in U.S. Pat. No. 6,407,079 to Muller et al., (hereby incorporated by reference herein in its entirety) of Formula (III):

$$(\beta\text{-CD})\text{-}(OR)_{21} \quad \text{(III)}$$

wherein R groups are independently selected from hydrogen, hydroxyalkyl or alkyl (e.g. methyl, ethyl and propyl) and wherein at least one R group is hydroxyalkyl (e.g. hydroxyethyl, hydroxypropyl or dihydroxypropyl).

β-cyclodextrin is a compound with ring structure consisting of 7 anhydro glucose units; it is also referred to as cycloheptaamylose. Each of the 7 glucose rings contains in 2-, 3-, and 6-position three hydroxy groups which may be etherified. Therefore, a total of 21 hydroxy groups per cyclodextrin molecule are available for etherification. In the partially etherified β-cyclodextrin derivatives suitable for the present invention only a portion of these available hydroxy groups are etherfied with hydroxyalkyl groups. Optionally a portion of these available hydroxy groups are etherfied with alkyl groups. In the hydroxyalkyl ethers of β-cyclodextrin used in accordance with the invention the average degree of substitution (DS) with hydroxyalkyl groups per cyclodextrin molecule is about 0.5 to about 20, about 2 to about 18 or about 3 to about 16.

Partially etherified β-cyclodextrin which comprises alkyl groups in addition to hydroxyalkyl groups, optionally have a degree of substitution per cyclodextrin molecule of about 0.35 to about 16 or about 1.4 to about 15.

In another embodiment the cyclodextrins are hydroxyethyl, hydroxypropyl and dihydroxypropyl ether cyclodextrins, their corresponding mixed ethers, and further mixed ethers with methyl or ethyl groups, such as methyl-hydroxyethyl, methyl-hydroxypropyl, ethyl-hydroxyethyl, and ethyl-hydroxypropyl ether of β-cyclodextrin.

Preparation of hydroxyalkyl ethers of β-cyclodextrin can be carried out using any suitable method, for example methods described in U.S. Pat. No. 3,459,731 to Gramera et al., hereby incorporated herein in its entirety.

In another embodiment, the β-cyclodextrin is a partially alkylated β-cyclodextrin, for example a partially methylated or partially dimethylated β-cyclodextrin. Partially alkylated β-cyclodextrins preferably have an average degree of substitution (DS) with alkyl groups per cyclodextrin molecule of about 0.5 to about 20, about 2 to about 18 or about 3 to about 16, for example about 14.

In another embodiment, the cyclodextrin is selected from those described in U.S. Pat. No. 5,134,127 and has a structure represented by Formula (IV):

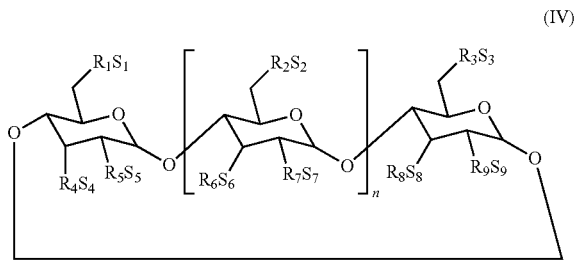

wherein:

n is 4, 5, or 6;

$R_1$, $R_2$, $R_3$, $R_4$, $R_5$, $R_6$, $R_7$, $R_8$ and $R_9$ are each, independently, $O^-$ or a $O$—$C_{2-6}$-alkylene)-$SO_3^-$ group, wherein at least one of $R_1$ and $R_2$ is independently a $O$—$(C_{2-6}$-alkylene)-$SO_3^-$ group, or a $O$—$(CH_2)_m SO_3^-$ group, wherein m is 2 to 6 or 2 to 4, (e.g. $OCH_2CH_2CH_2SO_3^-$ or $OCH_2CH_2CH_2CH_2SO_3^-$); and $S_1$, $S_2$, $S_3$, $S_4$, $S_5$, $S_6$, $S_7$, $S_8$, and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the $C_{1-6}$ alkylamines, piperidine, pyrazine, $C_{1-6}$ alkanolamine and $C_{4-8}$ cycloalkanolamine.

In one embodiment, $R_1$ is a $O$—$(C_{26}$-alkylene)-$SO_3^-$ group, or a $O$—$(CH_2)$ $mSO_3^-$ group (e.g. $OCH_2CH_2CH_2SO_3^-$ or $OCH_2CH_2CH_2CH_2SO_3$) wherein m is 2-6 or 2-4;

$R_2$ to $R_9$ are $O^-$;

$S_1$ to $S_9$ are each, independently, a pharmaceutically acceptable cation.

In another embodiment, $R_1$, $R_2$ and $R_3$ are each, independently, a $O$—$(C_{2-6}$-alkylene)-$SO_3^-$ group or a $O$—$(CH_2)_m SO_3^-$ group, (e.g. $OCH_2CH_2CH_2SO_3^-$ or $OCH_2CH_2CH_2SO_3^-$) wherein m is 2-6 or 2-4;

$R_4$ to $R_9$ are $O^-$; and $S_1$ to $S_9$ are each, independently, a pharmaceutically acceptable cation.

In yet another embodiment, $R_1$ to $R_3$ are each, independently, a $O$—$(C_{2-6}$-alkylene)-$SO_3^-$ group;

at least one of $R_4$, $R_6$ and $R_9$ is a $O$—$(C_{2-6}$-alkylene)-$SO_3^-$ group, for example a $O$—$(CH_2)_m SO_3$— group wherein m is 2-6 or 2-4 (e.g., $OCH_2CH_2CH_2SO_3^-$ or $OCH_2CH_2 CH_2CH_2SO_3^-$);

$R_5$, $R_7$ and $R_9$ are $O^-$; and $S_1$ to $S_9$ are each, independently, a pharmaceutically acceptable cation.

In another embodiment: $R_1$, $R_2$, $R_3$, $R_4$, $R_6$ and $R_9$ are each, independently, a $O$—$(C_{2-6}$-alkylene)-$SO_3^-$ group, for example a $O$—$(CH_2)mSO_3$— group wherein m is 2-6 or 2-4 (e.g. $OCH_2CH_2CH_2CH_2SO_3^-$ or $OCH_2CH_2CH_2SO_3$);

$R_5$, $R_7$ and $R_9$ are $O^-$; and $S_1$ to $S_9$ are each, independently, a pharmaceutically acceptable cation.

In another embodiment, the cyclodextrin is a sulfoalkyl-ether β-cyclodextrin, for example sulfobutylether-β-cyclodextrin having an average substitution of about 4 to about 8 or about 5 to about 7, for example about 6.4 sulfobutyl ether linkages (i.e. sulfobutyl ether$_{6.4}$-β-cyclodextrin).

One or more cyclodextrins, if desired, are present in a composition of the invention in an amount of at least about 2.5% (w/v), at least about 5% (w/v), at least about 7.5% (w/v), at least about 10% (w/v), at least about 12.5% (w/v), at least about 15% (w/v), or at least about 20% (w/v). Illustratively, a cyclodextrin is present in a total amount of about 5% to about 95% (w/v), about 5% to about 80% (w/v), about 7.5% to about 75% (w/v), about 10% to about 60% (w/v), about 15% to about 50% (w/v), or about 20% to about 50% (w/v).

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; water for injection, Ringer's solution, isotonic sodium chloride solution, fixed oils such as synthetic mono- and diglycerides and the like. Such diluents, if present, constitute in total about 5% to about 99%, about 10% to about 85%, or about 20% to about 80%, of the total weight of the composition.

Compositions of the invention optionally comprise one or more pharmaceutically acceptable disintegrants as excipients. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums. Such disintegrants, if present, typically comprise in total about 0.2% to about 30%, about 0.2% to about 10%, or about 0.2% to about 5%, of the total weight of the composition.

Compositions of the invention optionally comprise one or more antioxidants or anti-microbial agents. Illustrative antioxidants include sodium ascorbate and vitamin E (tocopherol). Illustrative anti-microbial agents include parabens, chlorobutanol, phenol, and sorbic acid. One or more antioxidants or anti-microbial agents, if present, are typically present in a composition of the invention in an amount of about 0.001% to about 5%, about 0.005% to about 2.5%, or about 0.01% to about 1%, by weight.

Compositions of the invention optionally comprise one or more pharmaceutically acceptable binding agents or adhesives as excipients. Such binding agents and adhesives can impart sufficient cohesion to a powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including antiadherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the composition. Glidants can be used to promote powder flow of a solid formulation. Suitable glidants include colloidal silicon dioxide, starch, talc, tribasic calcium phosphate, powdered cellulose and magnesium trisilicate.

Compositions of the invention optionally comprise a suspending agent. Non-limiting illustrative examples of suitable suspending agents include silicon dioxide, bentonite, hydrated aluminum silicate (e.g. kaolin) and mixtures thereof. One or more suspending agents are optionally present in compositions of the invention in a total amount of about 0.01% to about 3.0%, about 0.1% to about 2.0%, or about 0.25% to about 1.0%, by weight The foregoing excipients can have multiple roles as is known in the art. For example, starch can serve as a filler as well as a disintegrant. The classification of excipients above is not to be construed as limiting in any manner. Excipients categorized in any manner may also operate under various different categories of excipients as will be readily appreciated by one of ordinary skill in the art.

In another embodiment, upon storage in a closed container maintained at either room temperature, refrigerated (e.g. about 5-10° C.) temperature, or freezing temperature for a period of about 1, 6, or 12 months or longer, pharmaceutical compositions as disclosed herein exhibit at least about 90%, at least about 95%, or at least about 99% of the original glycoside(s) present therein.

Therapeutic Methods

In one embodiment, the present invention provides methods of treating or preventing a variety of cancers including, without limitation, colorectal, non-small cell, lung, ovarian, breast, colon, CNS, liver, lung, and kidney cancers. The methods comprise administering a therapeutically effective amount of a glycoside compound as disclosed herein (or pharmaceutical composition comprising such a compound) to a subject in need thereof. The related terms "therapeutically effective amount," "prophylactically effective amount," "effective amount" or "amount effective to treat" as used herein refer to an amount of glycoside that is sufficient to elicit the required or desired therapeutic and/or prophylactic response, as the particular treatment context may require.

The term "treating" in relation to a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder.

The term "prevention" in relation to a given disease or disorder means preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, a pharmaceutical composition as disclosed herein is administered to a subject in need of treatment in an amount sufficient to provide a daily glycoside compound dose of about 0.1 mg to about 10 g, about 1 mg to about 5 g, or about 25 mg to about 2.5 g, for example about 0.1 mg, about 0.5, about 1 mg, about 5 mg, about 10 mg, about 50 mg, about 100 mg, about 150 mg, about 250 mg, about 500 mg, about 750 mg, about 1000 mg, about 1500 mg, about 2000 mg, about 2500 mg, about 5000 mg, about 7500 mg, or about 9000 mg.

In another embodiment, a pharmaceutical composition as disclosed herein is administered to a subject in need of treatment in an amount sufficient to provide a daily glycoside compound dose of about 0.01 microgram (μg) per kilogram (kg) body weight (μg/kg) to about 100 mg/kg body weight (mg/kg), about 0.01 μg/kg to about 50 mg/kg, about 0.01 μg/kg to about 25 mg/kg, about 0.1 μg/kg to about 10 mg/kg, or about 1 μg/kg to about 5 mg/kg.

A pharmaceutical composition as disclosed herein can be administered to a subject one to a small plurality of times per day to achieve the above daily glycoside dosing. The term "small plurality" herein means more than one but less than about 5. For example, a small plurality in the present context could illustratively represent about 2 or 3.

Equivalent glycoside compound dosages to those disclosed above may be administered over various time periods including, but not limited to, about every 2 hours, about every 8 hours, about every 12 hours, about every 24 hours, about every 48 hours, about every 72 hours, about every week, about every two weeks, about every three weeks, about every month, and about every two months.

It is not critical whether a glycoside compound as disclosed herein is administered directly to a target cell, to a tissue that includes a target cell, to a body fluid that contacts a target cell, or to a body location from which the glycoside can diffuse or be transported to a target cell. It is sufficient that the glycoside is administered to the patient in an amount and by a route whereby a sufficient amount of the glycoside arrives, directly or indirectly, at the target cell(s). The minimum amount varies with the identity of the glycoside being administered. In one embodiment, a useful minimum amount is from about 10-9 molar to about 10-5 molar, or even from about 10-7 molar to about 10-5 molar.

In one embodiment, compounds of the invention are useful in treatment of tumors that are refractory to conventional antitumor drugs. Such tumors can be solid tumors with hypoxic regions and any tumor resistant to therapy with conventional antitumor drugs.

In addition to use in the treatment of cancer, compounds of the invention can be used in the treatment of cystic fibrosis. At non-toxic concentrations compounds as disclosed herein are believed to inhibit IL-8 secretion by cystic fibrosis lung cells and partially restore the ion-transport function of the CFTR protein lost in cystic fibrosis, giving them significant potential as safe and effective new drugs for treatment of this disease.

Compounds disclosed herein are also useful in the treatment of diseases caused by calcium oscillations because they can be administered at therapeutically effective doses that cause little or no inhibition of Na,K+ flux. These oscillations can activate the calcium-dependent transcription factor NF-κB that mediates the expression of several anti-apoptotic genes which can protect kidney cells from serum deprivation induced apoptosis. Abnormal calcium homeostasis is linked to the pathogenesis of many diseases, and in accordance with the methods of the invention, cardiac glycosides are administered as a new therapy for calcium-related pathologies (Aperia, *Journal of Internal Medicine.* 261:44-52, 2007).

The compounds of the invention also can be administered to act as neuroprotective agents in the CNS, as it is known that other cardiac glycosides can protect rat hearts against ischaemia-reperfusion injury (Prassas and Diamandis, *Nat Rev Drug Discov.* 7:926-35, 2008). Accordingly, the present invention provides methods for treatment of stroke and heart ischemia by administering therapeutically effective doses of compounds or pharmaceutical compositions of the invention to a subject in need thereof.

The invention also provides methods of treatment of other non-cancer hyperproliferative diseases characterized by cellular hyperproliferation (e.g., an abnormally increased rate or amount of cellular proliferation). In one embodiment, the hyperproliferative disease treated according to the present method is selected from the group consisting of allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, derniatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, scrum sickness, surgical adhesions, stenosis or restenosis, scleritis, schleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis. Use of a compound of the invention in manufacture of a medicament for treating any of the foregoing diseases is also provided by the present invention.

In some embodiments of the invention, a compound of the present invention is administered to treat a hyperproliferative disease selected from the group consisting of psoriasis, multiple sclerosis, rheumatoid arthritis, restenosis, and benign prostatic hyperplasia. In one embodiment, the hyperproliferative disease treated is psoriasis, a disease characterized by the cellular hyperproliferation of keratinocytes which builds up on the skin to form elevated, scaly lesions. In another embodiment, the hyperproliferative disease treated is multiple sclerosis, a disease characterized by progressive demyelination in the brain. In another embodiment, the hyperproliferative diseases treated is rheumatoid arthritis, a multisystem chronic, relapsing, inflammatory disease that can lead to destruction of joints affected. In another embodiment, a compound of the present invention is administered to prevent a hyperproliferative disease resulting from cellular proliferation on a prosthesis implanted in a subject by coating the prosthesis with a composition containing a compound of the present invention. In another embodiment, the hyperproliferative disease treated is benign prostatic hyperplasia, a disease in which prostate epithelial cells grow abnormally and thereby block urine flow.

In addition to the above therapeutic methods, the glycosides disclosed herein are also suitable for use in other applications including, e.g., as diagnostic or research tools and in the discovery of other biologically active compounds. Use of a compound of the invention in manufacture of a medicament for treating any of the foregoing diseases is also provided by the present invention.

Combination Therapy

Glycosides as disclosed herein can be administered as a sole therapeutic agent, in combination with other glycosides, or in combination with one or more other pharmaceutically active compounds. Combination agents can be selected to treat the same disease as the glycoside or a different disease. If the subject is to receive or is receiving multiple pharmaceutically active compounds, the compounds can be administered simultaneously, substantially simultaneously or sequentially in any order. The compounds also can be administered in the same or different dosage units, the same or different dosage forms (e.g., delivering at least one compound in the form of a tablet and delivering a second compound in the form of an injection or a syrup that is delivered orally) and/or the same or different routes of administration (e.g. one agent by oral delivery route and a second agent by intravenous delivery route).

In one embodiment, when glycosides are administered in combination with additional antiproliferative agent(s) for the treatment of cancer and/or for inhibiting the formation of metastases, such antiproliferative agent(s) can include, without limitation, those agents disclosed herein below.

In one embodiment, a glycoside compound of the instant invention is added to an existing clinical regimen (e.g. paclitaxel for the treatment of breast cancer). In another embodiment, addition of a glycoside to an existing clinical regiment acts to provide one or more of the following benefits: (a) reducing the minimum efficacious dose of one or both agents; (b) reducing adverse reactions or side effects of one or both agents; (c) improving efficacy of one or both agents; (d) extending the life of the subject being treating; and/or (e) improving cure rate.

In such combination therapy embodiments, the dosage and frequency of administration of the glycoside and additional anti-proliferative agent(s) can be controlled independently. For example, one compound may be administered orally three times per day, while the second compound may be administered intravenously once per day. The compounds may also be formulated together such that one dosage unit contains both compounds.

The exemplary dosage of the glycoside and additional antiproliferative agent(s) to be administered will depend on such variables as the type and extent of the disorder, the overall health status of the patient, the therapeutic index of the selected antiproliferative agent(s), and their route of administration. Standard clinical trials may be used to optimize the dose and dosing frequency for any particular combination of the invention.

Alkylating Agents
Nitrogen Mustards.
Mechlorethamine (Hodgkin's disease, non-Hodgkin's lymphomas); Cyclophosphamide, Ifosfamide (Acute and chronic lymphocytic, leukemias, Hodgkin's disease, non-Hodgkin's lymphomas, multiple myeloma, neuroblastoma, breast, ovary, lung, Wilms' tumor, cervix, testis, soft-tissue, Sarcomas); Melphalan (Multiple mycloma, breast, ovary); Chlorambucil (Chronic lymphocytic leukemia, Primary macroglobulincmia, Hodgkin's disease, non-Hodgkin's lymphomas); Uracil mustard (Leukemia); Estramustinc (Solid Tumors)
Ethylenimines and Methylmelamines.
Mitomycin C (Colorectal, ocular); AZQ (Primary brain tumors); Thiotepa (Bladder, breast, ovary)
Alkyl Sulfonates.
Busulfan, Hepsulfan (Chronic myelogenous leukemia)
Nitrosoureas.
Carmustine (Hodgkin's disease, non-Hodgkin's lymphomas, primary brain tumors, multiple myeloma, malignant melanoma); Lomustine (Hodgkin's disease, non-Hodgkin's lymphomas, primary brain tumors, small cell lung); Semustine (Primary brain tumors, stomach, colon); Streptozocin (Malignant pancreatic insulinama, malignant carcinoid)
Triazines.
Dacarbazine (Malignant melanoma, Hodgkin's disease, soft-tissue sarcomas)
Platinum Complexes.
Cisplatin, Carboplatin (Testis, ovary, bladder, head and neck, lung, thyroid, cervix, endometrium, neuroblastoma, osteogenic sarcoma)
Methyl Hydrazine Derivative.
Procarbazine (Hodgkin's disease)
Antimetabolites
Folic Acid Antagonists.
Methotrexate, Trimetrexate (Acute lymphocytic leukemia, choriocarcinoma, mycosis fungoides, breast, head and neck, lung, osteogenic sarcoma)

Pyrimidine Antagonists.
Fluorouracil, Floxuridine (Breast, colon, stomach, pancreas, ovary, head and neck, urinary bladder, skin, adenocarcinomas); Cytarabine (Acute myelogenous and acute lymphocytic leukemias); Fludarabine Phosphate (Lymphoproliferative disease); Capecitabine (Breast, renal cell, prostate); Azacitidine (acute leukemias)
Purine Antagonists.
Thioguanine (Acute myelogenous, acute lymphocytic and chronic myelogenous leukemias); Mercaptopurine (Acute lymphocytic, acute myelogenous and chronic myelogenous leukemias); Allopurine (leukemias); Cladribine (Hairy cell leukemia); Gemcitabine (Pancreatic, soft tissue carcinomas); Pentostatin (Hairy cell leukemia, mycosis fungoides; chronic lymphocytic leukemia)
Antimitotic Agents
Vinblastine (Hodgkin's disease, non-Hodgkin's lymphomas, breast, testis); Vincristine (Acute lymphocytic leukemia, neuroblastoma, Wilms' tumor, rhabdomyosarcoma, Hodgkin's disease, non-Hodgkin's lymphomas, small-cell lung)
DNA Topoisomerase II Inhibitors
Etoposidc, Teniposide (Testis, small-cell lung, oat-cell lung, breast, Hodgkin's disease, non-Hodgkin's lymphomas, acute myclogenous leukemia, Kaposi's sarcoma)
DNA Topoisomerase I Inhibitors
Topotecan, Irinotecan Camptothecin, 9-Amino-Camptothecin (Ovarian, colorectal)
Taxanes
Paclitaxel, Docetaxel (Breast)
DNA Intercalators
Daunorubicin (Acute myelogenous and acute lymphocytic leukemias); Doxorubicin (myosarcomas, Hodgkin's disease, non-Hodgkin's lymphomas, acute leukemias, multiple myeloma, breast, genitourinary, thyroid, lung, ovarian, endometrial, testicular, stomach, neuroblastoma); Dactinomycin (Choriocarcinoma, Wilms' tumor, rhabdomyosarcoma, testis, Kaposi's sarcoma); Idarubicin (Acute myeloid leukemia); Plicamycins (Testicular cancer); Mitomycin (Squamous sell carcinomas, small bladder, papillomas adenocarcinomas, pancreas, lung, colon, stomach, cervix, breast, head and neck); Amsacrine (Acute myelogenous leukemia, ovarian cancer, lymphomas); Bleomycin (Testicular, head and neck, skin, esophagus, squamous cell, colorectal, lung, genitourinary tract, cervix, ovarian, breast, Hodgkin's disease, non-Hodgkin's lymphomas)
Hormonal Agents
Aromatase Inhibitors.
Aminogluthimide Anastrozole (Breast)
5-Alpha-Reductase Inhibitors.
Finasteride, Ketoconazole (Prostate)
Estrogen and Androgen Inhibitors.
Tamoxifen (Breast); Flutamide (Prostate)
Gonadotropin Releasing Hormone Agonists.
Leuprolide, Goserelin (Prostate)
Tyrosine Kinase Inhibitors
ABL Inhibitors.
Gleevec (chronic myelogenous leukemia or acute lymphoblastic leukemia)
PDGFR Inhibitors.
Leflunomide, SU5416, SU6668, PTK787 (gastrointestinal stromal tumor, small cell lung cancer, glioblastoma multifome, and prostate cancer)
EGFR Inhibitors.
Iressa, Tarceva, trastuzumab, Erbitux, PK1166, GW2016, EKB-509, EKB-569, MDX-H210, 2C4, MDX-447, ABX-EGF, CI-1033 (non-small-cell lung cancer, breast cancer, ovarian cancer, bladder cancer, prostate cancer, salivary gland cancer, pancreatic cancer, endometrial cancer, colorectal cancer, kidney cancer, head and neck cancer, glioblastoma multiforme)

VEGFR Inhibitors.

Avastin, IMC-ICII, ZD4190, ZD6474 (any solid tumor)

Trk Inhibitors.

CEP-701, CEP-751 (prostate cancer, pancreatic cancer)

Flt-3 Inhibitors.

MLN518, PKC412 (acute myeloid leukemia)

Retinoic Acid Derivatives 13-cis-retinoic acid, isotretinoin, tretinyl palmitate, 4-(hydroxycarbphenyl) retinamide (Acute promyelocytic leukemia, head and neck squamous cell carcinoma)

Hypoxia-Selective Cytotoxins

Misonidazole (head and neck); Nitracrine (breast)

Miscellaneous Agents

Mitoxantrone (Acute myelogenous leukemia non-Hodgkin's lymphoma's, breast); Hydroxyurea (Chronic myelogenous leukemia, polycythemia vera, essential thrombocytosis, malignant melanoma); L-asparagine (Acute lymphocytic leukemia); Interferon alfa (Hairy cell leukemia, Kaposi's sarcoma, melanoma, carcinoid, renal cell, ovary, bladder, non-Hodgkin's lymphomas, mycosis fungoides, multiple myeloma, chronic myelogenous leukemia); Rapamycin, CCI-779 (Glioblastoma Multiforme, renal cell carcinoma); Mitotane (Adrenal carcinoma)

The following examples are for illustrative purposes only and should not be construed as limiting the invention in any manner.

EXAMPLES

Example 1

Synthesis of Isodigitoxigenin Glycosides

Digitoxigenin 1: Digitoxin (10 g, 13.07 mmol) was suspended in methanol (300 mL), p-toluene sulfonic acid (1.02 g, 1.31 mmol) was added and stirred overnight at room temperature. Methanol was removed under reduced pressure, residue dissolved in acetone, precipitated with hexanes, and filtered to give digitoxigenin 1 as a white solid (3.86 g, 79% yield). $^1$H-NMR (CDCl$_3$, 300 MHz): 5.87 (X of ABX, J=1.5 Hz, 1H), 4.99 (A of ABX, J=18.1, 1.5 Hz, 1H), 4.80 (B of ABX, J=18.1, 1.5 Hz, 1H), 4.13 (br s, 1H), 2.78 (m, 1H), 2.23-2.06 (m, 2H), 1.98-1.14 (m, 20H), 0.96 (s, 3H), 0.88 (s, 3H)

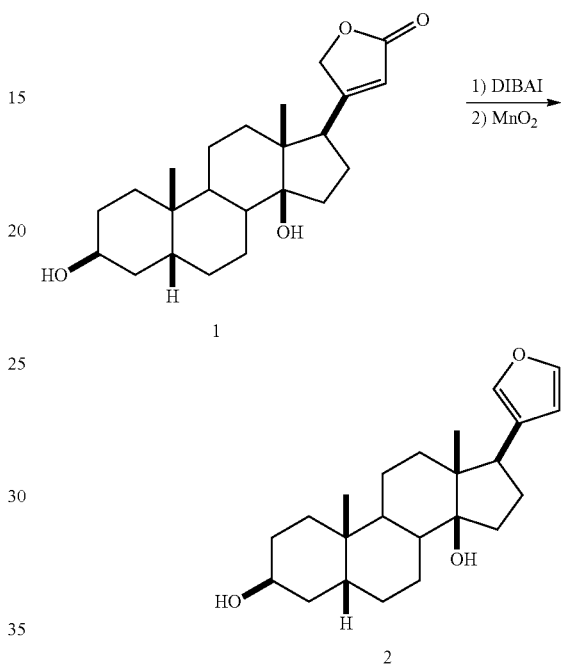

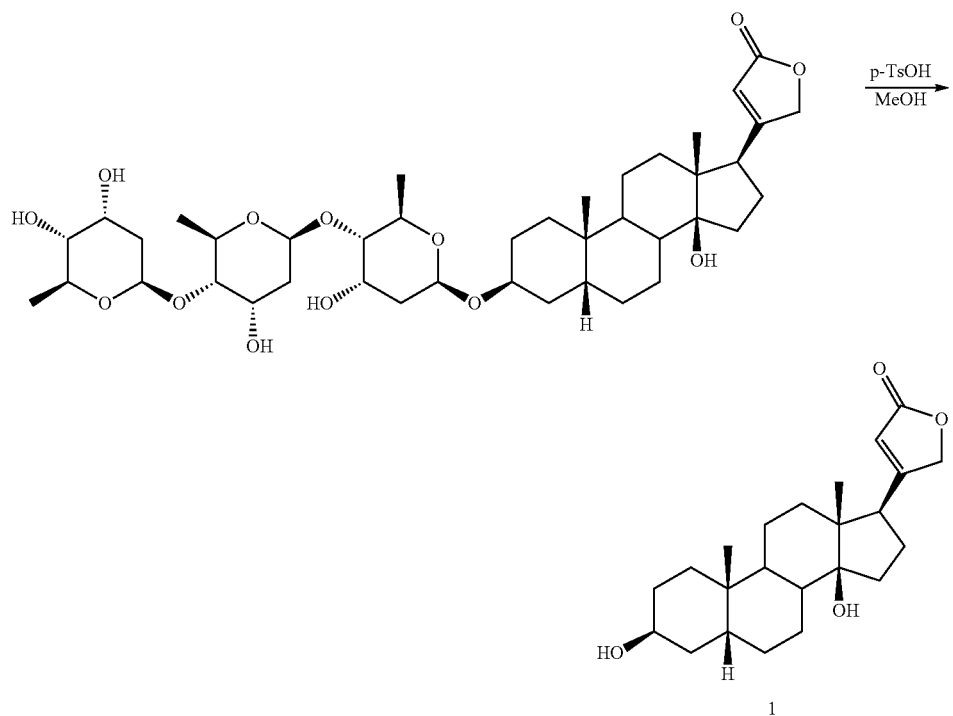

Furan 2: Digitoxigenin 1 (2.50 g, 6.68 mmol) was dissolved in THF and cooled to −5° C. DIBAL (60.1 mL of 1M solution in THF, 60.1 mmol) was added dropwise via addition funnel. The solution was stirred for 1.5 h when it was poured into 10% H$_2$SO$_4$. EtOAc was added and the aqueous layer was washed with ethyl acetate. The combined organic layers were washed with saturated NaHCO$_3$, dried (Na$_2$SO$_4$), and concentrated. The crude product was dissolved in dioxane/H$_2$O/AcOH (20 mL/4 mL/2 mL) and MnO$_2$ (5.81 g, 66.8 mmol) was added. The solution was heated to 80° C. and stirred for 2.5 h. The solution was filtered through Celite® and concentrated. The crude solid was dissolved in dichloromethane and washed with saturated NaHCO$_3$. The organic layer was dried (Na$_2$SO$_4$) and concentrated. The crude product was purified by silica gel chromatography. Yield, 2=1.76 g (74%): $^1$H NMR (CDCl$_3$, 300 MHz) δ 7.31 (dd, J=1.5, 1.5 Hz, 1H), 7.20 (dd, J=0.73, 0.73 Hz, 1H), 6.46 (dd, J=1.8, 0.73 Hz, 1H), 4.14 (m, 1H), 2.74 (dd, J=9.5, 5.9 Hz, 1H), 1.1-2.1 (m, 21H), 0.95 (s, 3H), 0.71 (s, 3H); $^{13}$C NMR (CDCl$_3$, 75 MHz) δ 142.7, 139.9, 129.8, 112.3, 86.1, 67.2, 48.3, 47.2, 42.7, 40.8, 36.5, 36.0, 35.8, 33.7, 33.0, 30.0, 29.8, 28.3, 26.9, 24.1, 21.8, 21.7, 16.8.

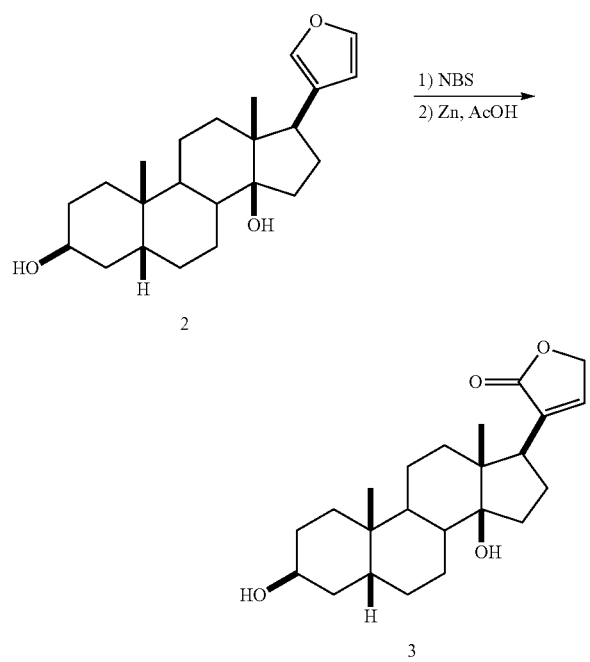

Isodigitoxigenin 3: The furan 2 (600 mg, 1.67 mmol) was dissolved in dioxane/H$_2$O (20 mL, 20:1). Sodium acetate (192 mg, 2.34 mmol) and NBS (328 mg, 1.84 mmol) were added. The solution was stirred for 1.5 h, then chloroform and saturated NaHCO$_3$ were added. The layers were split and the aqueous layer was extracted with chloroform. The organic layer was dried (Na$_2$SO$_4$) and concentrated. The crude solid was dissolved in acetic acid (5 mL) and 150 mg zinc dust was added. The suspension was stirred for 30 min when it was filtered and washed with ethyl acetate. This solution was concentrated and purified by silica gel chromatography (1:1 hexanes:EtOAc to 2:1 EtOAc:hexanes). The product was dissolved in EtOAc and washed with 1M Na2CO3 six times to remove succinimide. Yield 3=432 mg (69%): $^1$H NMR (CDCl$_3$, 300 MHz) δ 7.26 (m, 1H), 4.79 (m, 2H), 4.13 (m, 1H), 2.77 (dd, J=7.3, 7.3 Hz, 1H), 1.1-2.1 (m, 21H), 0.95 (s, 3H), 0.82 (s, 3H); $^{13}$C NMR (CDCl$_3$, 75 MHz) δ 175.8, 147.7, 137.3, 85.6, 70.4, 67.1, 49.1, 47.4, 41.7, 41.1, 36.3, 35.6, 35.6, 33.6, 33.1, 29.9, 28.1, 27.1, 26.8, 24.0, 21.7, 21.6, 15.9.

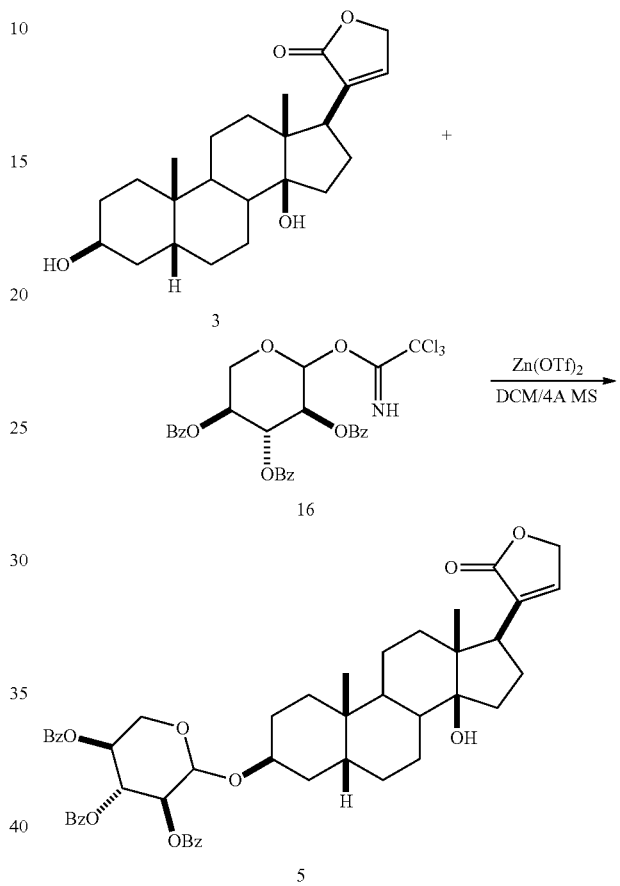

Benzoylated Isodigitoxigenin Xyloside 5: Isodigitoxigenin 3 (7.13 g, 19.9 mmol) and Zn(OTf)$_2$ (361 mg, 0.99 mmol) were placed in a round bottom flask with dichloromethane (70 mL) and molecular sieves and then cooled to 0 to 5° C. The imidate 16 (14.48 g, 23.86 mmol) was dissolved in dichloromethane (50 mL) and added dropwise. The solution was stirred for 3 h when ethyl acetate and sat. NaHCO$_3$ were added. The solution was split and the organic layer was washed with brine. The organic layer was then dried (Na$_2$SO$_4$) and concentrated. The crude product was purified by silica gel chromatography (20:1 DCM:acetone). Yield 5=10.67 g (66%) iso-digitoxin xyloside+1.2 g iso-digitoxigenin: $^1$H NMR (CDCl$_3$, 300 MHz) δ 7.99 (m, 6H), 7.51 (m, 3H), 7.36 (m, 6H), 7.25 (m, 1H), 5.76 (dd, J=7.3, 7.3 Hz, 1H), 5.39 (dd, J=7.0, 5.5 Hz, 1H), 5.30 (ddd, J=7.0, 7.0, 4.4 Hz, 1H), 4.87 (d, J=5.5 Hz, 1H), 4.78 (br s, 2H), 4.44 (dd, J=12.0, 4.0 Hz, 1H), 4.07 (br s, 1H), 3.69 (dd, J=12.0, 7.3 Hz, 1H), 2.74 (m, 1H), 2.1-1.0 (m, 22H), 0.78 (s, 3H), 0.63 (s, 3H); $^{13}$C NMR (CDCl$_3$, 75 MHz) δ 175.9, 165.9, 165.8, 165.5, 147.6, 137.5, 133.7, 133.7, 133.5, 130.2, 130.1, 129.7, 129.5, 129.4, 128.7, 128.7, 128.6, 98.0, 85.8, 73.7, 70.8, 70.7, 70.5, 69.6, 61.5, 49.1, 47.4, 41.9, 41.0, 36.7, 35.9, 35.3, 33.2, 32.4, 29.9, 27.3, 26.9, 24.1, 23.7, 21.8, 21.6, 15.9.

CEN08-193

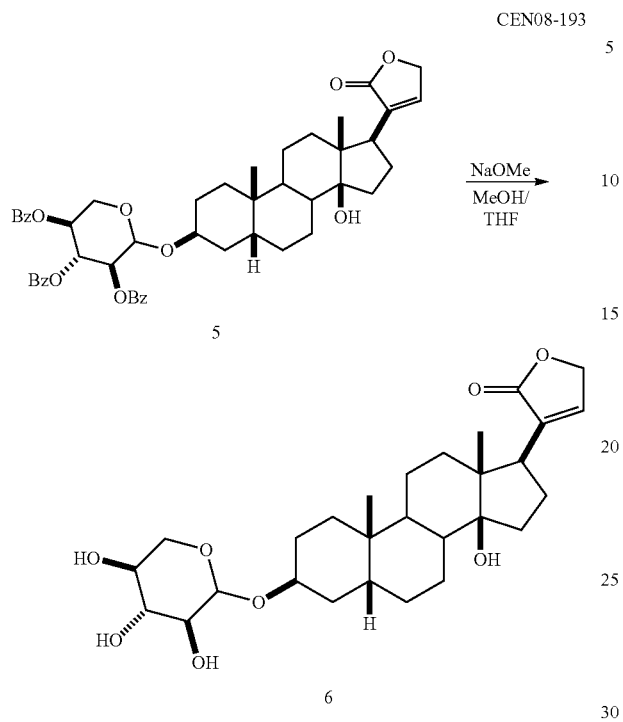

Isodigitoxigenin Xyloside 6: The tri-benzoate 5 (50 mg, 0.061 mmol) was suspended in methanol/THF (60 mL MeOH:20 mL THF) and NaOMe (0.29 mL of 25% solution) was added. The solution was stirred for 4 h when Amberlite acidic resin was added. The resin was filtered and the solution was concentrated. The crude product was purified by silica gel chromatography (9:1 DCM:MeOH) Yield 6=4.83 g (76%): $^1$H NMR (CD$_3$OD, 300 MHz) δ 7.47 (br s, 1H), 4.87 (m, 2H), 4.29 (d, J=7.3 Hz, 1H), 4.03 (br s, 1H), 3.85 (dd, J=11.3, 5.1 Hz, 1H), 3.47 (ddd, J=10.2, 8.8, 5.1 Hz, 1H), 3.30 (m, 1H), 3.16 (m, 2H), 2.70 (m, 1H), 2.2-1.1 (m, 22H), 0.94 (s, 3H), 0.79 (s, 3H); $^{13}$C NMR (CDCl$_3$, 75 MHz) δ 176.1, 149.0, 137.3, 102.7, 85.0, 77.5, 74.2, 73.6, 71.2, 70.5, 66.5, 49.1, 46.4, 41.9, 41.9, 36.9, 35.9, 35.7, 33.0, 32.6, 30.5, 28.9, 27.4, 24.7, 24.5, 22.0, 21.9, 16.5.

Example 2

Synthesis of Digitoxigenin O-Glycosides

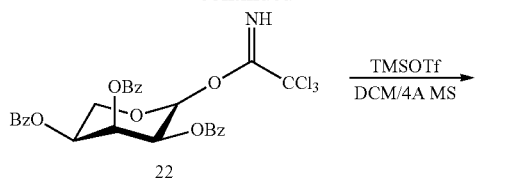

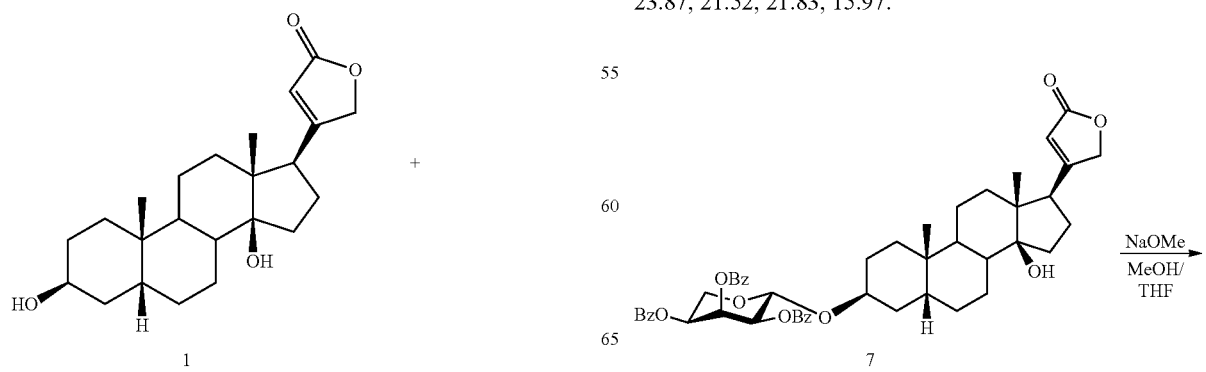

Digitoxigenin tri-benzoyl-O-L-Riboside 7: Digitoxigenin 1 (9.46 g, 25.3 mmol) was dissolved in DCM (150 mL) containing 4 Å molecular sieves and brought to 0° C. under an atmosphere of Argon. To this solution was added α/β-1-tricholoracetaimidate-2,3,4-tri-benzoyl-L-ribose (16.86 g, 27.8 mmol) and stirred for 5 min, followed by the addition of trimethylsilyl trifluoromethanesulfonate (228 μL, 1.26 mmol). The reaction was stirred at 0° C. for 15 min. then filtered, sieves were washed with DCM (100 mL), and the solvent removed in vacuo. The reaction mixture was purified by flash chromatography (8:2 Hexanes:EtOAc to EtOAc) to give 7 as a white foam (17.0 g, 20.7 mmol, 82%). $^1$H-NMR (CDCl$^3$, 300 MHz): δ 8.02 (ddd, J=13.5, 7.6, 1.1 Hz, 4H), 7.89 (dd, J=7.6, 1.1, 2H), 7.58-7.46 (m, 3H), 7.37-7.25 (m, 6H), 5.91-5.83 (m, 2H), 5.63 (q, J=3.2 Hz, 1H), 5.49 (t, J=3.0 Hz, 1H), 5.22 (d, J=2.6 Hz, 1H), 5.02 (A of ABX, J=18.3, 1.1 Hz, 1H), 4.80 (B of ABX, J=18.3, 1.1 Hz, 1H), 4.36-4.03 (m, 3H), 2.85-2.71 (m, 1H), 2.21-1.13 (m, 22H), 0.93 (s, 3H), 0.87 (s, 3H) $^{13}$C-NMR (CDCl$_3$, 75 MHz): δ 175.27, 174.84, 166.39, 166.23, 165.54, 133.48, 133.37, 130.16, 130.10, 130.01, 129.90, 129.66, 128.58, 128.55, 117.67, 96.36, 85.47, 73.72, 72.83, 69.63, 68.03, 66.85, 61.48, 51.18, 49.88, 41.87, 36.84, 35.87, 35.43, 33.23, 32.16, 30.19, 27.10, 23.98, 23.87, 21.52, 21.83, 15.97.

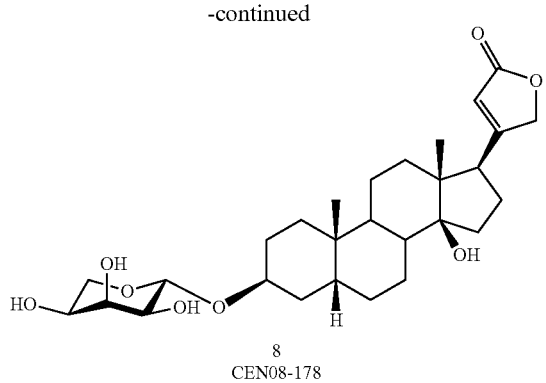

8
CEN08-178

Digitoxigenin O-L-Riboside 8: Digitoxigenin tri-benzoyl-O-L-Riboside 7 (9.0 g, 11.0 mmol) was dissolved in 3:1 methanol:THF (300 mL) at room temperature. Sodium methoxide (250 uL of 25% solution) was added, and stirred for 3 h. Acetic acid (70 μL) was added and stirred for 1 min, then the solvent was removed in vacuo. The resulting residue was purified by silica gel flash chromatography (DCM to 9:1 DCM:MeOH) to give 8 as a white solid (4.5 g, 8.89 mmol, 80%). $^1$H-NMR (DMSO-d$_6$/CD$_3$OD, 300 MHz): δ 5.85 (X of ABX, J=1.6 Hz, 1H), 4.94 (A of ABX, J=18.5, 1.6 Hz, 1H), 4.83 (B of ABX, J=18.5, 1.6 Hz, 1H), 4.61 (d, J=4.2 Hz, 1H), 3.84 (br s, 1H), 3.66 (t, J=2.9 Hz, 1H), 3.62-3.54 (m, 2H), 3.47 (dd, J=12.0, 6.0 Hz, 1H), 3.33 (dd, J=4.2, 2.9 Hz, 1H), 2.70 (m, 1H), 2.11-1.93 (m, 2H), 1.91-0.99 (m, 20H), 0.85 (s, 3H), 0.75 (s, 3H) $^{13}$C-NMR (DMSO-d$_6$/CD$_3$OD, 75 MHz): δ 177.08, 174.54, 116.88, 99.21, 84.4, 73.78, 72.19, 71.78, 69.36, 67.56, 64.33, 50.92, 50.05, 41.60, 37.05, 35.51, 35.46, 32.78, 32.26, 30.47, 27.06 (br), 24.18, 21.64, 21.46, 16.40.

Example 3

Synthesis of Scillarenin Neo-Glycosides

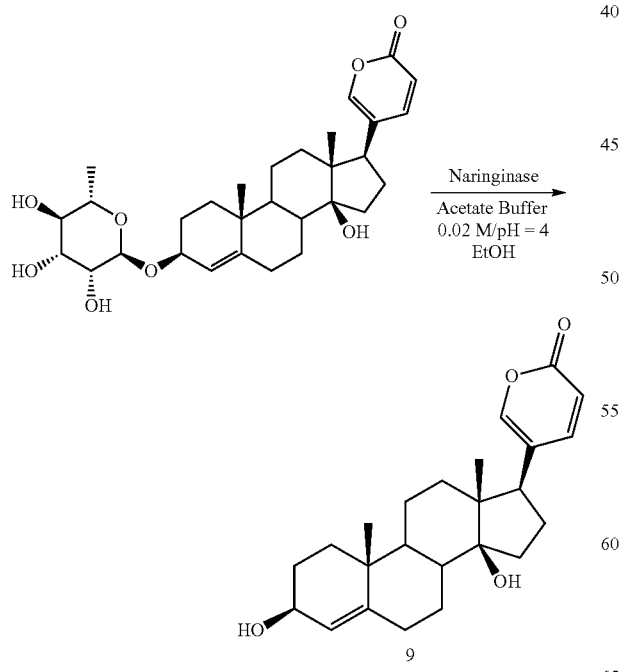

Scillarenin 9: Proscillaridin (3 g, 5.6 mmol) was dissolved in ethanol (57 ml) at 40° C. while stirring, to this solution was added 171 ml of sodium acetate buffer (pH=4, 0.02 M) at 40° C., followed by naringinase (1.03 g). The reaction was stirred for 24 hours, when ethanol was added (200 ml) and the solvent was removed in vacuo, an additional 100 ml ethanol was added and the solvent was removed in vacuo. Material was purified by flash chromatography (DCM to 9:1 DCM:MeOH) to give 9 as an off-white solid (1.9 g, 4.9 mmol, 90%). $^1$H-NMR (CDCl$_3$, 300 MHz): 7.89 (dd, J=9.7, 2.6 Hz, 1H), 7.26 (dd, J=2.6, 0.9 Hz, 1H), 6.27 (dd, J=9.7, 0.9, 1H), 5.31 (s, 1H), 4.31 (m, 1H), 2.47 (dd, J=9.3, 6.2 Hz, 1H), 2.25-0.98 (m, 19H), 1.04 (s, 3H), 0.73 (s, 3H) $^{13}$C-NMR (CDC$_{13}$, 75 MHz): 163.28, 148.77, 147.59, 146.42, 123.90, 123.35, 115.22, 85.01, 67.65, 51.20, 50.38, 48.46, 42.65, 40.82, 37.58, 35.71, 32.65, 32.36, 29.17, 28.89, 28.76, 21.43, 19.10, 16.69.

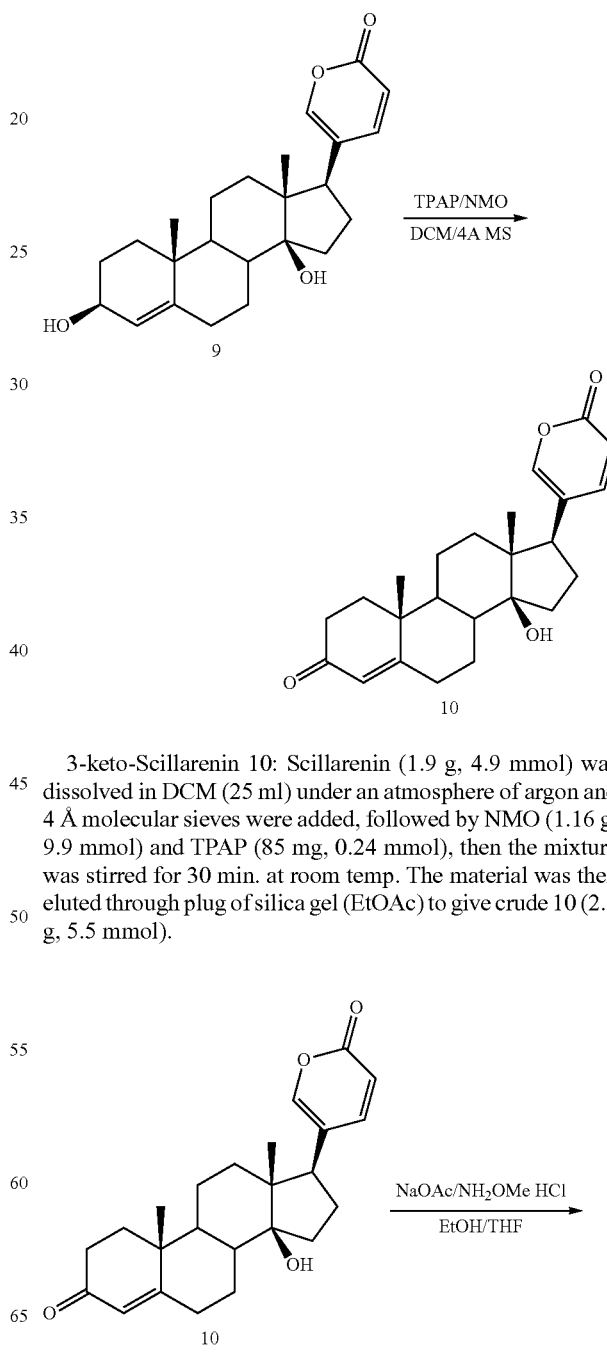

3-keto-Scillarenin 10: Scillarenin (1.9 g, 4.9 mmol) was dissolved in DCM (25 ml) under an atmosphere of argon and 4 Å molecular sieves were added, followed by NMO (1.16 g, 9.9 mmol) and TPAP (85 mg, 0.24 mmol), then the mixture was stirred for 30 min. at room temp. The material was then eluted through plug of silica gel (EtOAc) to give crude 10 (2.1 g, 5.5 mmol).

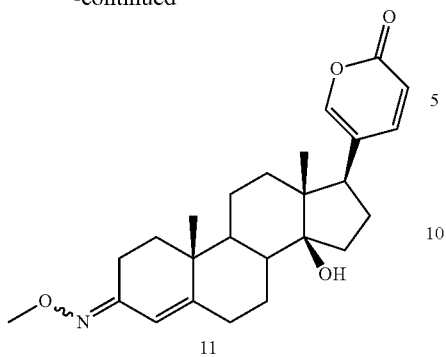

Scillarenin oximes 11: Crude 10 (2.1 g, 5.5 mmol) was dissolved in 3:1 ethanol:THF (50 ml); to the resulting solution was added methoxyamine hydrochloride (2.3 g, 27.5 mmol) and sodium acetate (1.35 g, 16.5 mmol). The solution was stirred at room temperature for 30 min. Solvent was removed in vacuo and the residue was purified by flash chromatography (4:1 Hexanes:EtOAc to 35:65 Hexanes:EtOAc) to give a mixture of oximes 11 as a white solid (1.39 g, 3.37 mmol, 61%).

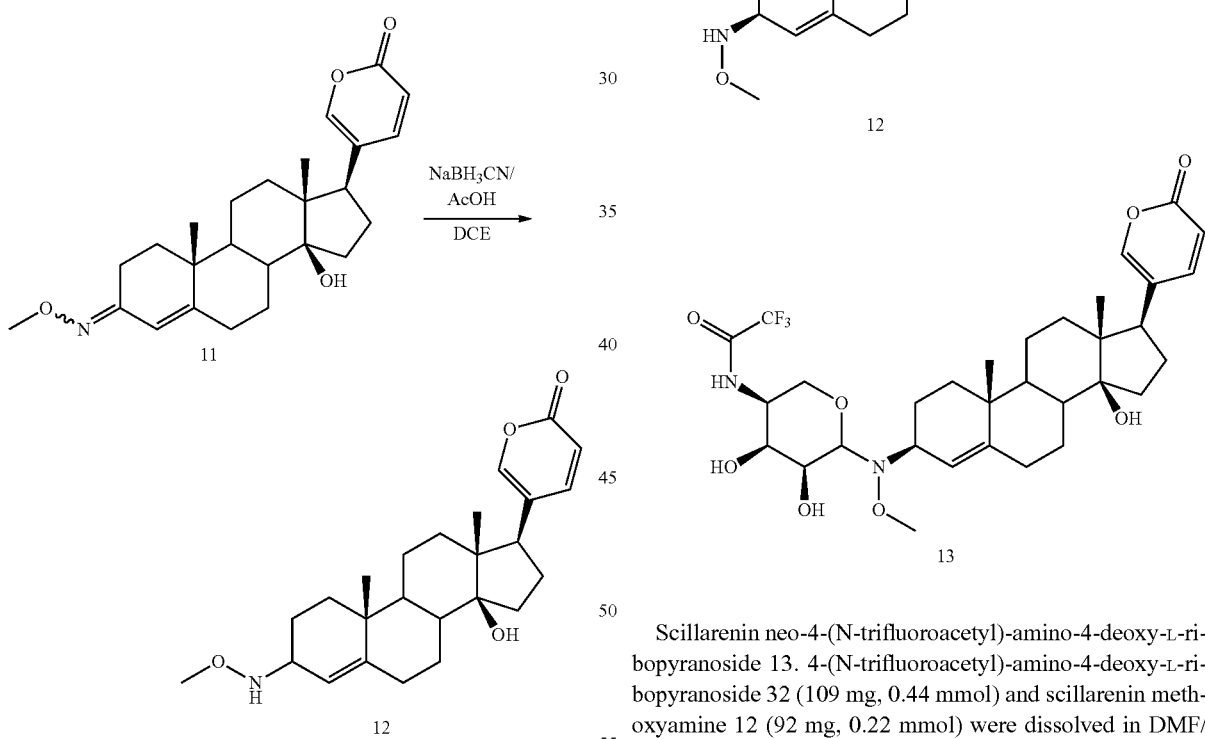

Scillarenin methoxyamine 12: Scillarenin oximes 11 (1.39 g, 3.37 mmol) were dissolved in 25 ml dicholoroethane with stirring. NaBH$_3$CN (2.1 g, 33.7 mmol) and acetic acid (1.93 ml, 33.7 mmol) were added and the mixture was stirred for 45 min, at which time a solution of saturated NaHCO$_3$ (20 ml) was added. Dichloromethane (300 ml) was added and the organic layer was washed with: saturated NaHCO$_3$ (50 ml) and brine (100 ml), dried over Na$_2$SO$_4$ and concentrated in vacuo. The residue was purified by flash chromatography (3:2 Hexanes:EtOAc to 2:3 Hexanes:EtOAc) to yield 12 as a white foam (556 mg, 13.5 mmol, 40%). $^1$H-NMR (CDCl$_3$, 300 MHz): 7.83 (dd, J=9.7, 2.6 Hz, 1H), 7.23 (dd, J=2.6, 0.9 Hz, 1H), 6.26 (dd, J=9.7, 0.9 Hz, 1H), 5.30 (s, 1H), 3.58-3.47 (m, 4H), 2.46 (dd, J=9.5, 6.4 Hz, 1H), 2.27-0.97 (m, 19H), 1.03 (s, 3H), 0.73 (s, 3H).

Scillarenin neo-4-(N-trifluoroacetyl)-amino-4-deoxy-L-ribopyranoside 13. 4-(N-trifluoroacetyl)-amino-4-deoxy-L-ribopyranoside 32 (109 mg, 0.44 mmol) and scillarenin methoxyamine 12 (92 mg, 0.22 mmol) were dissolved in DMF/AcOH (3.1 mL, 3:1). The reaction mixture was stirred for 3 days at 35° C. The solvents were removed under reduced pressure. The residue was purified by flash chromatography (CH$_2$Cl$_2$/MeOH, 95:5) to afford scillarenin neo-4-(N-trifluoroacetyl)-amino-4-deoxy-L-ribopyranoside 13 as a yellow foam (80 mg, 56%) R$_f$ 0.30 (CH$_2$Cl$_2$/MeOH, 90:10). $^1$H-NMR (300 MHz, C$_5$D$_5$N) δ 0.95 (s, 6H, CH$_3$), 1.00-2.48 (m, 18H), 3.94 (s, 3H, NOCH$_3$), 4.19 (m, 2H), 4.45 (m, 1H), 4.75 (m, 2H), 4.96 (m, 2H), 5.06 (d, 1H, J=7.5 Hz), 5.41 (s, 1H), 5.84 (s, 1H), 6.38 (d, 1H, J=9.7 Hz), 7.48 (s, 1H), 8.25 (dd, 1H, J=2.1, 9.3 Hz).

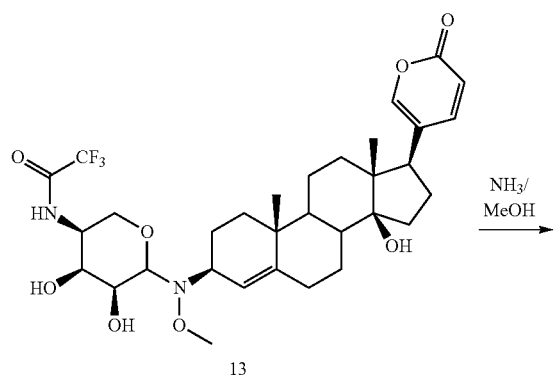

13

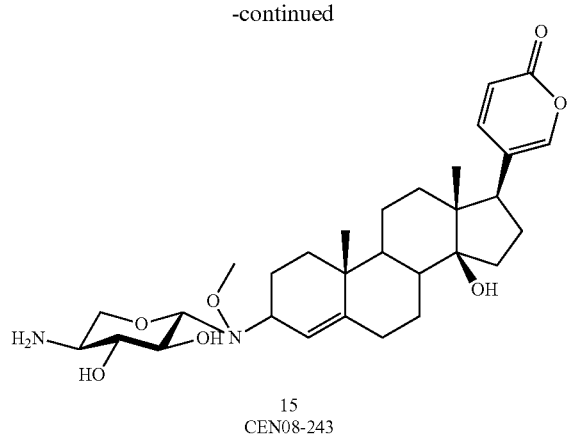

15
CEN08-243

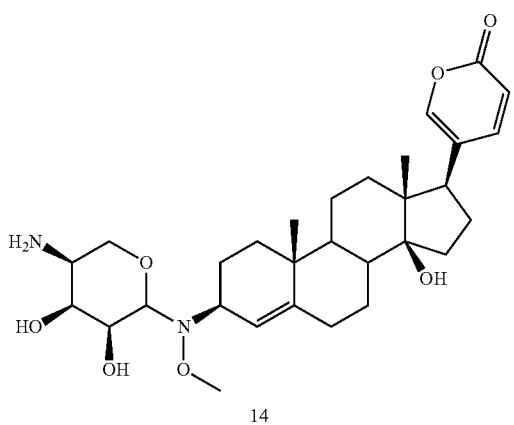

14

Scillarenin neo-4-amino-4-deoxy-L-ribopyranoside 14. Scillarenin neo-4-(N-trifluoroacetyl)-amino-4-deoxy-L-ribopyranoside 13 (810 mg, 1.26 mmol) was dissolved in 30% aq. NH$_3$/MeOH (15:85). The reaction mixture was stirred overnight. The solvents were removed under reduced pressure. The residue was purified by flash chromatography (CH$_2$Cl$_2$/MeOH/NH$_3$, 94.8:5:0.2 to 89.8:10:0.2) to afford 14 as a yellow solid (430 mg, 62%) R$_f$ 0.13 (CH$_2$Cl$_2$/MeOH/NH$_3$, 89.8:10:0.2).

Scillarenin neo-4-amino-4-deoxy-L-Xyloside 15: Scillarenin methoxyamine 12 (30 mg, 0.072 mmol) and 4-amino-4-deoxy-L-xylose 37 (25.4 mg, 0.14 mmol) were dissolved in 3:1 DMF:AcOH (1.0 mL) and reacted at 40° C. for 36 hours. Solvent was removed in vacuo, the residue was eluted through silica gel plug with 95:4.5:0.5 DCM:MeOH:NH$_4$OH then evaporated, to remove unreacted sugar, and the resulting residue was dissolved in 9:1 THF:water (1 mL). To the solution was added triphenylphosphine (38.0 mg, 0.14 mmol) and the reaction was stirred at room temperature for 6 hours. Solvent was removed in vacuo, and the residue was purified by flash silica gel chromatography (95:4.5:0.5 DCM:MeOH:NH$_4$OH to 80:19:1 DCM:MeOH:NH$_4$OH) to give 15 as a white solid (4.4 mg, 0.008 mmol, 11%). $^1$H-NMR (CD$_3$OD, 300 MHz): δ 7.85 (dd, J=9.7, 2.5 Hz, 1H), 7.24 (dd, J=2.5, 0.7 Hz, 1H), 6.27 (dd, J=9.7, 0.7, 1H), 5.40 (s, 1H), 3.99 (d, J=8.8 Hz, 1H), 3.95 (dd, J=11.3, 5.0 Hz, 1H), 3.78-3.59 (m, 5H), 3.29 (t, J=8.8 Hz, 1H), 3.09 (t, J=11.3 Hz, 1H), 2.92 (ddd, J=11.3, 8.8, 5.0 Hz, 1H), 2.47 (dd, J=9.3, 6.3 Hz, 1H), 2.23-0.99 (m, 19H), 1.03 (s, 3H), 0.73 (s, 3H).

Example 4

Synthesis of Sugars

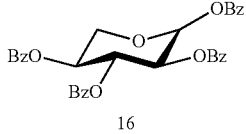

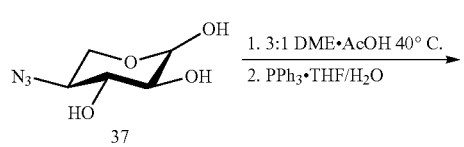

16

Tetra-benzoyl-L-Xylose 16: L-Xylose (5.0 g, 33.3 mmol) was suspended in pyridine (45 mL, 556 mmol) at 0° C., benzoyl chloride (30.9 mL, 26.6 mmol) was added over 15 min., and stirred for an additional 30 min. The solvent was removed in vacuo, the residue was dissolved in dichloromethane (300 mL) and the solution washed 3 times with 200 mL 1 M HCl, saturated NaHCO$_3$ (150 mL), brine (150 mL), then dried over Na$_2$SO$_4$, and concentrated in vacuo, to yield 16 as a thick yellow oil (18.03 g, 31.8 mmol, 95%). Material was used without further purification.

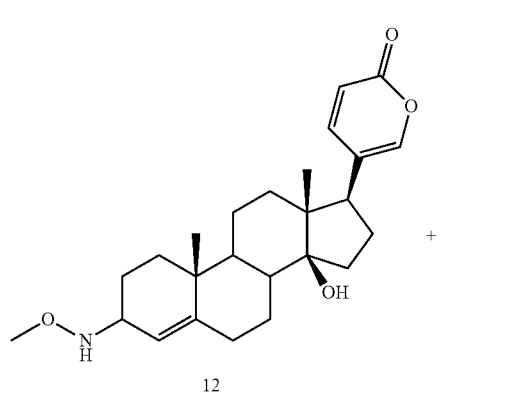

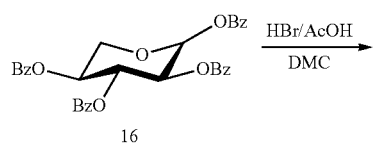

16

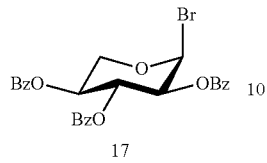

17

1-bromo-2,3,4-tri-benzoyl-L-Xylose 17: Crude tetra-benzoyl-L-xylose 16 (18 g, 31.7 mmol) was dissolved in dichloromethane (175 mL) under an atmosphere of argon at 0° C. To this solution was added 33% HBr in AcOH (34.5 mL, 190.2 mmol of HBr) and the reaction was stirred for 30 min. at 0° C. then brought to room temperature for 30 min. Dichloromethane (100 mL) was added, then the mixture was washed with 125 mL of cold water, dilute NaHCO₃, two times with saturated NaHCO₃, brine, then dried over Na₂SO₄ and concentrated in vacuo to yield 16 as an off-white solid (14.1 g, 26.8 mmol, 85%). This material was used without further purification.

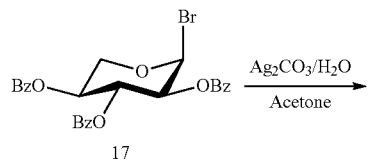

18

2,3,4-tri-benzoyl-L-Xylose 18: Crude 1-bromo-2,3,4-tri-benzoyl-L-xylose 17 (14.1 g, 26.8 mmol) was dissolved in acetone (150 mL) and water (5 ml, 277 mmol) at 0° C. Silver carbonate (6.61 g, 24.0 mmol) was added over 5 min and the reaction was brought to room temperature after 15 min and stirred an additional 30 min. The solids were removed by filtration and washed with acetone (100 mL), the filtrate was concentrated in vacuo, water was removed via azeotropic distillation with ethanol and toluene and the residue was purified by silica gel flash chromatography (4:1 Hexanes: EtOAc to EtOAc) to yield 18 as white solid (9.1 g, 19.6 mmol, 74%).

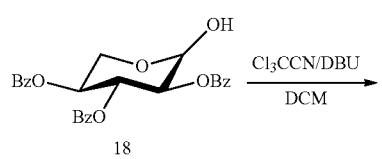

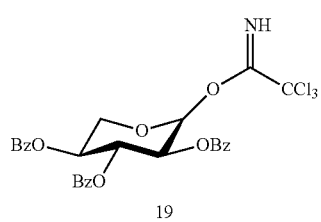

19

α/β-1-tricholoracetaimidate-2,3,4-tri-benzoyl-L-Xylose 19 2,3,4-tri-benzoyl-L-xylose 18 (1.0 g, 2.2 mmol) was dissolved in 15 mL dichloromethane at 0° C.; to this solution was added trichloroacetonitrile (2.6 mL, 25.9 mmol) and DBU (1.6 μL, 0.11 mmol). The reaction was stirred at 0° C. for 30 min., then concentrated in vacuo and purified by silica gel flash chromatography (DCM) to give 19 as a white solid (1.2 g, 1.98 mmol, 92%)

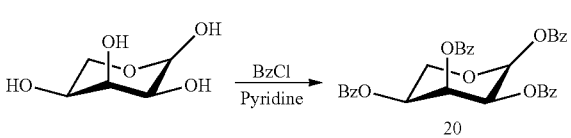

20

Tetra-benzoyl-L-Ribose 20: L-Ribose (4.8 g, 31.9 mmol) was suspended in pyridine (45 mL, 556 mmol) at 0° C., benzoyl chloride (29.7 mL, 25.6 mmol) was added over 15 min and the reaction was stirred for an additional 30 min. Solvent was removed in vacuo and the residue was dissolved in dichloromethane (300 mL) and washed 3 times with 200 mL 1 M HCl, saturated NaHCO₃ (150 mL) and brine (150 mL), then dried over Na₂SO₄, and concentrated in vacuo, to give 20 as a thick yellow oil (17.0 g, 30.0 mmol, 94%). This material was used without further purification.

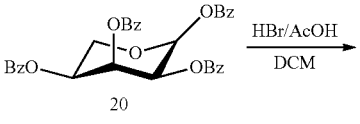

20

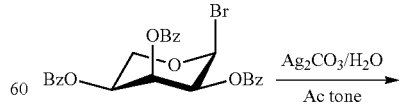

21

1-bromo-2,3,4-tri-benzoyl-L-Ribose 21: Crude tetra-benzoyl-L-ribose 20 (17.0 g, 30.0 mmol) was dissolved in dichloromethane (150 mL) under an atmosphere of argon at 0° C. To this solution was added 33% HBr in AcOH (32.6 mL, 180.0 mmol of HBr) and the reaction was stirred for 30 min at 0° C. then brought to room temperature for 30 min. Dichloromethane (150 mL) was added and the reaction mixture was washed with 125 mL of cold water, dilute NaHCO₃, two times with saturated NaHCO₃ and brine then dried over Na₂SO₄ and concentrated in vacuo to give 21 as a off-white solid (13.3 g, 25.3 mmol, 84%). This material was used without further purification.

21

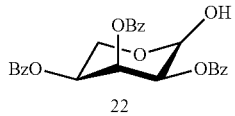

22

2,3,4-tri-benzoyl-L-Ribose 22: Crude 1-bromo-2,3,4-tri-benzoyl-L-ribose 21 (13.3 g, 25.3 mmol) was dissolved in acetone (150 mL) and water (5 ml, 277 mmol) at 0° C. Silver carbonate (6.28 g, 22.7 mmol) was added over 5 min. The reaction was brought to room temperature after 15 min and stirred an additional 30 min. The solids were removed by filtration and washed with acetone (100 mL) and the filtrate was concentrated in vacuo. The water was removed via azeotropic distillation with ethanol and toluene and the residue was purified by silica gel flash chromatography (4:1 Hexanes: EtOAc to EtOAc) to give 22 as white solid (9.8 g, 21.2 mmol, 85%).

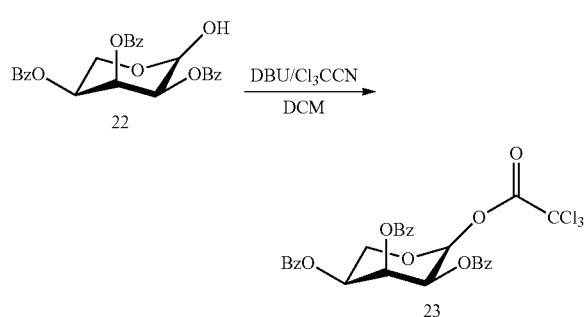

α/β-1-tricholoracetaimidate-2,3,4-tri-benzoyl-L-Ribose 23: 2,3,4-tri-benzoyl-L-ribose 22 (1.0 g, 2.2 mmol) was dissolved in 15 mL dichloromethane at 0° C.; to this solution was added trichloroacetonitrile (2.6 mL, 25.9 mmol) and DBU (1.6 μL, 0.11 mmol). The solution was stirred at 0° C. for 30 min, then it was concentrated in vacuo and purified by silica gel flash chromatography (DCM) to give 23 as a white solid (1.25 g, 2.06 mmol, 95%).

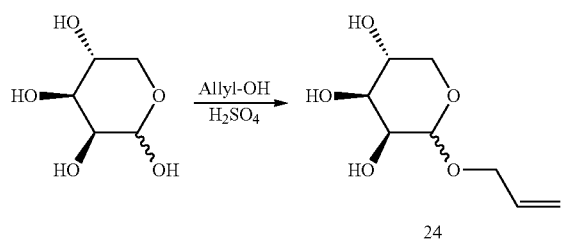

1-allyl-D-lyxopyranoside 24. To a suspension of D-Lyxose (50 g, 333 mmol) and Na$_2$SO$_4$ (50 g) in allyl alcohol (500 mL) at 0° C., H$_2$SO$_4$ (5.2 mL) was added dropwise. The reaction was heated at 85° C. and stirred for 12 h. The mixture was filtered and concentrated under reduced pressure. The crude material was purified by flash chromatography (CH$_2$Cl$_2$/MeOH, 95:5 to 80:20) to afford 1-allyl-D-lyxopyranoside 24 as a brown oil (50 g, 78%) R$_f$ 0.2 (CH$_2$Cl$_2$/MeOH, 9:1). $^1$H-NMR (300 MHz, CD$_3$OD) δ 3.44 (dd, 1H, J=10.6, 8.4 Hz, H-5), 3.60-3.71 (m, 4H, H-2, H-3, H-4, H-5), 3.99 (ddt, 1H, J=12.9, 6.3, 1.5 Hz, CH$_2$—CH═CH$_2$), 4.18 (ddt, 1H, J=12.9, 5.6, 1.5 Hz, CH$_2$—CH═CH$_2$), 4.71 (d, 1H, J=2.8 Hz, H-1), 5.17 (dq, 1H, J=10.2, 1.2 Hz, CH$_2$═CH), 5.28 (dq, 1H, J=17.1, 1.5 Hz, CH$_2$═CH), 5.93 (dddd, J=16.8, 10.5, 6.3, 5.7 Hz, CH$_2$═CH); $^{13}$C-NMR (75 MHz, CD$_3$OD) δ 63.0 (C-5), 67.3 (C-4), 68.0 (CH$_2$—CH═CH$_2$), 70.5, 71.6 (C-2, C-3), 99.9 (C-1), 116.2 (CH$_2$═CH), 134.3 (CH═CH).

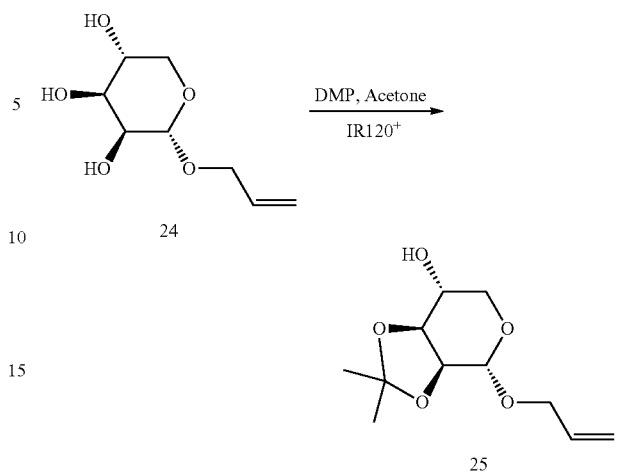

1-allyl-2,3-O-isopropylidene-D-lyxopyranoside 25. 1-allyl-D-lyxopyranoside 24 (50 g, 262 mmol) was dissolved in 2,2-dimethoxypropane/acetone (400 mL, 1:1) with 4-Å molecular sieves (73 g). At 0° C., IR 120$^+$ (13 g) was added and the mixture was stirred for 24 h at room temperature. The reaction mixture was filtered through a pad of Celite and concentrated under reduced pressure. The residue was purified by flash chromatography (Hexane/EtOAc, 3:2) to afford 1-allyl-2,3-O-isopropylidene-D-lyxopyranoside 25 as an off-white solid (33 g, 55%) R$_f$ 0.6 (Hexane/EtOAc, 1:1). $^1$H-NMR (300 MHz, CDCl$_3$) δ 1.36 (s, 3H), 1.51 (s, 3H), 3.67-3.76 (m, 1H, H-5), 3.78-3.87 (m, 2H, H-4, H-5), 4.07 (ddt, 1H, J=12.8, 6.2, 1.3 Hz, CH$_2$—CH═CH$_2$), 4.17 (dd, 1H, J=6.2, 2.7 Hz, H-2), 4.23-4.33 (m, 2H, H-3, CH$_2$—CH═CH$_2$), 4.81 (d, 1H, J=2.6 Hz, H-1), 5.23 (dq, 1H, J=10.5, 1.5 Hz, CH$_2$═CH), 5.32 (dq, 1H, J=17.3, 1.6 Hz, CH$_2$═CH); $^{13}$C-NMR (75 MHz, CDCl$_3$) δ 25.7 (CH$_3$), 27.7 (CH$_3$), 63.3 (C-5), 67.5 (C-4), 69.0 (CH$_2$—CH═CH$_2$), 74.6 (C-2), 76.4 (C-3), 97.8 (C-1), 109.7 (C(CH$_3$)$_2$), 118.3 (CH$_2$═CH), 133.6 (CH$_2$═CH).

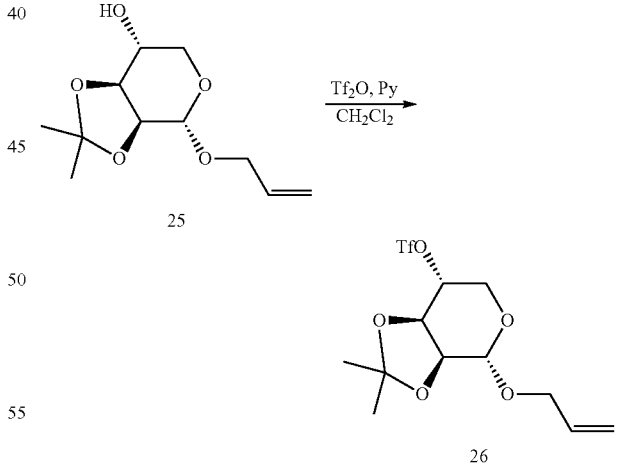

1-allyl-2,3-O-isopropylidene-4-trifluoromethanesulfonate-D-lyxopyranoside 26. 1-allyl-2,3-O-isopropylidene-D-lyxopyranoside 25 (33 g, 143 mmol) was dissolved in dry dichloromethane (300 mL) and pyridine (46 mL). Triflic anhydride (29 mL, 172 mmol) was added dropwise in 15 min at 0° C. The reaction was stirred for 20 min at 0° C. The reaction mixture was diluted with CH$_2$Cl$_2$ and washed with 1N HCl, a saturated solution of aq NaHCO$_3$ and brine. The organic layer was dried over Na$_2$SO$_4$, filtered and concentrated to give 1-allyl-2,3-O-isopropylidene-4-trifluoromethanesulfonate-D-lyxopyranoside 26 as an orange oil. The crude material was carried on without further purification. $R_f$ 0.7 (Hexane/EtOAc, 1:1).

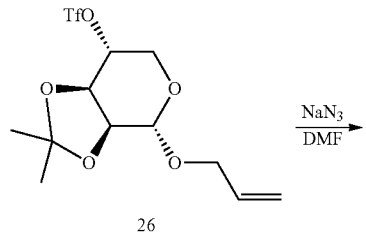

26

27

1-allyl-2,3-O-isopropylidene-4-azido-4-deoxy-L-ribopyranoside 27. Crude 1-allyl-2,3-O-isopropylidene-4-trifluoromethanesulfonate-D-lyxopyranoside 26 was dissolved in N,N-dimethylformamide (250 mL). NaN₃ was added and the mixture was stirred overnight at room temperature. The solvent was removed under reduced pressure, and the resulting residue was dissolved in dichloromethane and washed with water. The organic layer was dried over Na₂SO₄, filtered and concentrated. The crude was purified by flash chromatography (Hexane/EtOAc, 85:15 to 3:1) to give 1-allyl-2,3-O-isopropylidene-4-azido-4-deoxy-L-ribopyranoside 27 as a yellow oil (26.3 g, 72%) $R_f$ 0.5 (Hexane/EtOAc, 4:1). ¹H-NMR (300 MHz, CDCl₃) δ 1.40 (s, 3H), 1.57 (s, 3H), 3.72-4.41 (m, 6H, H-5), 3.78-3.87 (m, 2H, H-4, H-5), 4.56 (dd, 1H, J=6.2, 3.6 Hz), 4.67 (d, 1H, J=3.7 Hz, H-1), 5.18-5.39 (m, 2H), 5.83-5.99 (m, 1H); ¹³C-NMR (75 MHz, CDCl₃) δ 25.6 (CH₃), 26.9 (CH₃), 54.9 (C-4), 60.3 (C-5), 69.3 (CH₂—CH=CH₂), 73.0 (C-3), 75.4 (C-2), 98.6 (C-1), 110.8 (C(CH₃)₂), 118.0 (CH₂=CH), 133.8 (CH₂=CH).

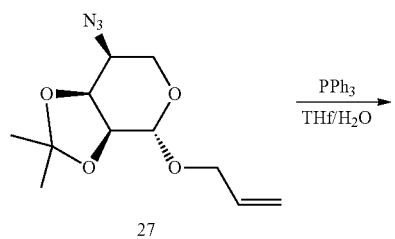

27

28

1-allyl-2,3-O-isopropylidene-4-amino-4-deoxy-L-ribopyranoside 28. 1-allyl-2,3-O-isopropylidene-4-azido-4-deoxy-L-ribopyranoside 27 (4.3 g, 16.8 mmol) was dissolved in THF/H₂O (60 mL, 9:1), PPh3 was added and the reaction mixture was stirred for 2 h at room temperature and to complete the reaction for 20 min at 50° C. The solvents were removed under reduced pressure and the crude material was carried on without further purification.

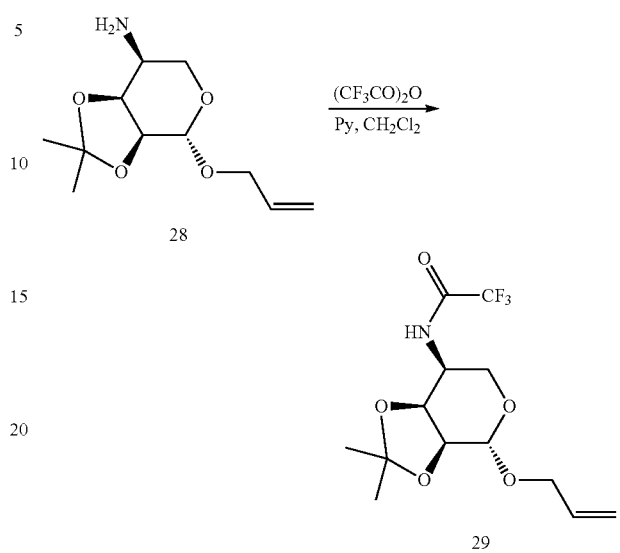

28

29

1-allyl-2,3-O-isopropylidene-4-(N-trifluoroacetyl)-amino-4-deoxy-L-ribopyranoside 29. Crude 1-allyl-2,3-O-isopropylidene-4-amino-4-deoxy-L-ribopyranoside 28 was dissolved in dichloromethane (60 mL). At 0° C., pyridine was added dropwise followed by dropwise addition of (CF₃CO)₂O. After stirring for 2 h at 0° C., the reaction mixture was poured into a saturated solution of aq NH₄Cl. The organic layer was washed with H₂O, brine, dried over Na₂SO₄, filtered and concentrated. The residue was purified by flash chromatography (light petroleum ether/EtOAc, 85:15 to 80:20) to give 1-allyl-2,3-O-isopropylidene-4-(N-trifluoroacetyl)-amino-4-deoxy-L-ribopyranoside 29 as an off-white foam (4.2 g, 77%) $R_f$ 0.4 (light petroleum/EtOAc, 4:1). ¹H-NMR (300 MHz, CDCl₃) δ 1.37 (s, 3H), 1.52 (s, 3H), 3.50 (dd, 1H, J=9.5, 10.7 Hz, H-5), 3.87 (dd, 1H, J=5.1, 10.8 Hz, H-5), 4.06 (ddt, 1H, J=12.9, 6.3, 1.2 Hz, CH₂—CH=CH₂), 4.15 (dd, 1H, J=3.5, 6.4 Hz, H-2), 4.8 (ddt, 1H, J=12.9, 5.1, 1.4 Hz, CH₂—CH=CH₂), 4.43 (dd, 1H, J=6.3, 4.3 Hz, H-3), 4.56 (dddd, 1H, J=9.5, 7.5, 4.5, 5.0 Hz, H-4), 4.70 (d, 1H, J=3.5 Hz, H-1), 5.22 (dq, 1H, J=10.4, 1.2 Hz, CH₂=CH), 5.32 (dq, 1H, J=17.2, 1.6 Hz, CH₂=CH), 5.90 (dddd, 1H, J=17.0, 11.4, 6.3, 5.1 Hz, CH₂=CH); ¹³C-NMR (75 MHz, CDCl₃) δ 25.4 (CH₃), 26.9 (CH₃), 45.3 (C-4), 60.1 (C-5), 69.2 (CH₂—CH=CH₂), 71.6 (C-3), 75.0 (C-2), 98.0 (C-1), 110.6 (C(CH₃)₂), 118.2 (CH₂=CH), 133.7 (CH₂=CH), 157.1 (CF₃CO).

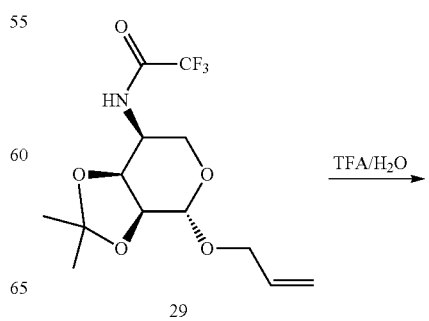

29

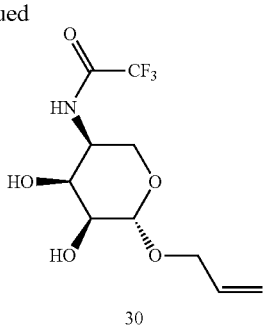

1-allyl-4-(N-trifluoroacetyl)-amino-4-deoxy-L-ribopyranoside 30. 1-allyl-2,3-O-isopropylidene-4-(N-trifluoroacetyl)-amino-4-deoxy-L-ribopyranoside 29 (4.2 g, 12.9 mmol) was dissolved in TFA/H$_2$O (30 mL, 80:20). The reaction mixture was stirred for 10 min at room temperature. The solvents are removed under reduced pressure and the resulting residue was purified by flash chromatography (CH$_2$Cl$_2$/MeOH, 95:5) to afford 1-allyl-4-(N-trifluoroacetyl)-amino-4-deoxy-L-ribopyranoside 30 as an off-white foam (3.68 g, 100%) R$_f$ 0.23 (CH$_2$Cl$_2$/MeOH, 95:5). $^1$H-NMR (300 MHz, CDCl$_3$) δ 3.64 (dd, 1H, J=12.0, 4.1 Hz, H-5), 3.84 (m, 1H, H-2), 3.92 (dd, 1H, J=2.2, 12.0 Hz, H-5), 4.0-4.06 (m, 1H, CH$_2$—CH=CH$_2$), 4.11 (dd, 1H, J=3.2 Hz, H-3), 4.21-4.29 (m, 2H, H-4, CH$_2$—CH=CH$_2$), 4.83 (d, 1H, J=2.9 Hz, H-1), 5.22-5.34 (m, 2H, CH$_2$=CH), 5.83-5.97 (m, 1H, CH$_2$=CH); $^{13}$C-NMR (75 MHz, CDCl$_3$) δ 49.8 (C-4), 61.5 (C-5), 65.6 (C-3), 69.1 (CH$_2$—CH=CH$_2$), 70.6 (C-2), 99.2 (C-1), 118.3 (CH$_2$=CH), 133.5 (CH$_2$=CH), 157.1 (CF$_3$CO).

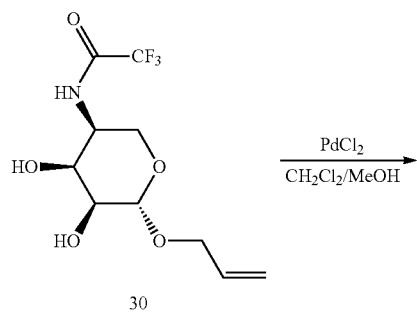

4-(N-trifluoroacetyl)-amino-4-deoxy-L-ribopyranoside 31. 1-allyl-4-(N-trifluoroacety)-amino-4-deoxy-L-ribopyranoside 30 was dissolved in dichloromethane/methanol (40 mL, 90:10) and PdCl$_2$ (0.5 g, 2.6 mmol) was added. The reaction mixture was stirred overnight at room temperature. The mixture was filtered through a pad of Celite and concentrated under reduced pressure. The residue was purified by flash chromatography (CH$_2$Cl$_2$/MeOH, 90:10 to 80:20) to afford 4-(N-trifluoroacetyl)-amino-4-deoxy-L-ribopyranoside 31 as brown dough (2.84 g, 90%) R$_f$ 0.12 (CH$_2$Cl$_2$/MeOH, 90:10). $^1$H-NMR (300 MHz, McOD) δ 3.62-3.67 (m, 2H), 4.00 (dd, 1H, J=11.7, 2.8 Hz), 4.04 (dd, 1H, J=3.5 Hz), 4.08 (dd, 1H, J=3.5 Hz), 5.01 (d, 1H, J=3.6 Hz, H-1).

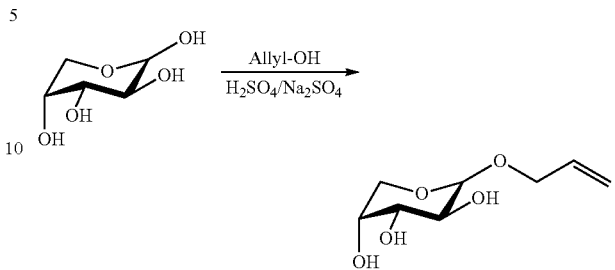

1-allyl-D-Arabinose 32: D-Arabinose (100 g, 666 mmol) and Na$_2$SO$_4$ (100 g, 703 mmol) were suspended in allyl alcohol (1 L, 14.65 mol) at room temperature; to this suspension was added concentrated H$_2$SO$_4$ (10.4 mL, 187 mmol). The reaction was stirred at 85° C. for 12 h, filtered, and the precipitate was washed with allyl alcohol (2 times 300 mL). The combined filtrates were concentrated in vacuo and purified by silica gel flash chromatography (DCM to 4:1 DCM:MeOH) to give 32 as an off-white solid (75 g, 394 mmol, 60%).

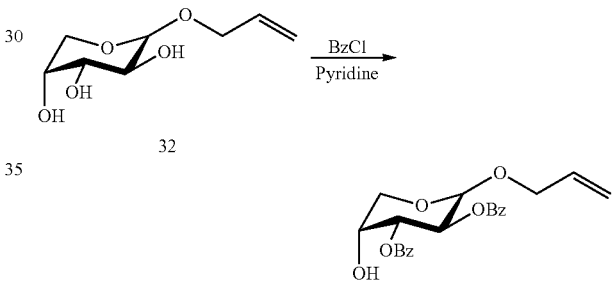

1-allyl-2,3-dibenzoyl-D-Arabinose 33: 1-allyl-D-arabinose 32 (75 g, 394 mmol) was dissolved in pyridine (800 mL) at 0° C., benzoyl chloride (101 mL, 867 mmol) was added over 2 h by addition funnel and the reaction was stirred while warming to room temperature for 16 h. The solvent was removed in vacuo, and the resulting residue was purified by silica gel flash chromatography (4:1 Hexanes:EtOAc to 3:2 Hexanes:EtOAc) to give 33 as a thick oil (45 g, 113 mmol, 29%).

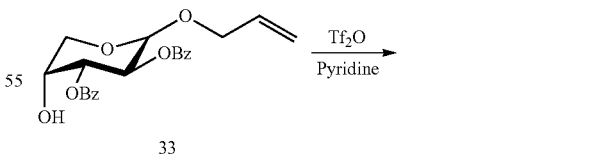

1-allyl-2,3-dibenzoyl-4-trifluoromethane sulfonate-D-Arabinose 34: 1-allyl-2,3-dibenzoyl-D-arabinose 33 (20.0 g, 50 mmol) was dissolved in DCM (100 mL) and pyridine (16.2 mL, 200 mmol) then triflic anhydride (10.6 mL, 62.7 mmol) was added and the reaction was stirred for 15 min at 0° C. To the reaction was added DCM (500 mL) and the organic layer was washed with cold 1M HCl (200 mL), saturated NaHCO$_3$ (200 mL), and brine (200 mL), then dried over Na$_2$SO$_4$. The mixture was concentrated in vacuo to give 34 as a yellow oil. The crude material was used without further purification.

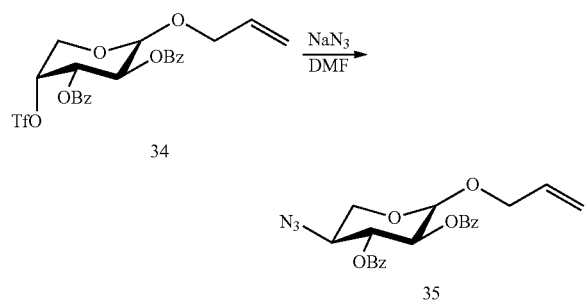

1-allyl-2,3-dibenzoyl-4-azido-4-deoxy-L-Xylose 35: Crude 1-allyl-2,3-dibenzoyl-4-trifluoromethanesulfonate-D-arabinose 34 was dissolved in N,N-dimethylformamide (100 mL), sodium azide was added (6.37 g, 98 mmol) and the reaction was stirred at room temperature for 18 h The solvent was removed in vacuo, the resulting residue was dissolved in DCM (750 mL), the organic layer was washed with water (two times 200 mL), brine (200 mL), then dried over Na$_2$SO$_4$ and concentrated in vacuo. The crude material was purified by silica gel flash chromatography (4:1 Hexanes:EtOAc to 3:2 Hexanes:EtOAc) to give 35 as a thick colorless oil (17.5 g, 41.3 mmol, 84%).

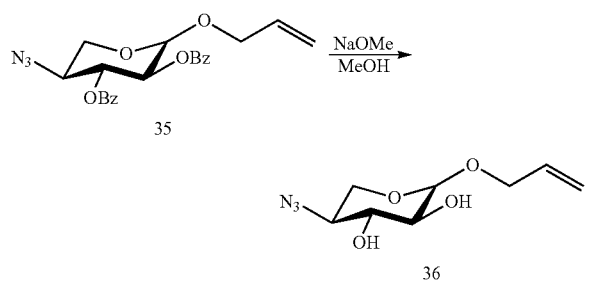

1-allyl-4-azido-4-deoxy-L-Xylose 36: 1-allyl-2,3-dibenzoyl-4-azido-4-deoxy-L-xylose 35 (12.0 g, 28.3 mmol) was dissolved in 5:1 methanol:THF (70 mL); to this solution was added sodium methoxide (650 µL of 25% solution, 2.83 mmol). The solution was stirred for 5 h, then to it was added acetic acid (175 µL, 3.11 mmol) and the reaction stirred for 1 min. The solvent was removed in vacuo to give 36 as a thick oil. The material was used without further purification.

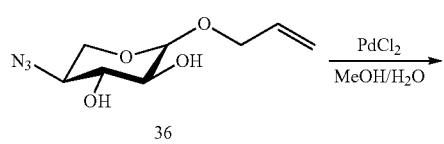

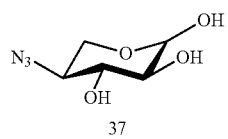

4-azido-4-deoxy-L-Xylose 37: 1-allyl-4-azido-4-deoxy-L-xylose 36 (496 mg, 2.3 mmol) was dissolved in 99:1 methanol:water (10 mL), followed by the addition of palladium (II) chloride (81.7 mg, 0.46 mmol). The reaction mixture was stirred for 24 h at room temperature, and then filtered through a pad of Celite® with methanol wash (100 mL). The combined filtrates were purified by silica gel flash chromatography (DCM to 9:1 DCM:MeOH) to give of 37 as a yellow oil (249 mg, 1.42 mmol, 62%).

Example 5

Cancer Cell Cytotoxicity Assay

Compounds of the invention and comparative compounds were assayed in three cancer cell lines to confirm cytotoxic activity and to set a range of concentrations to use in subsequent assays. All cell lines were maintained in RPMI medium 1640 supplemented with 10% (wt/vol) fetal bovine serum and penicillin-streptomycin (100 units/ml and 100 µg/ml). Cells were routinely checked for microbial or mycoplasma contamination and if necessary replaced. Cells were harvested by trypsinization using 0.25% trypsin and 0.1% EDTA and then counted in a ViCell XR coulter counter in duplicate, before and after dilution for assay plating. Between four to nine different types of human cancer cells were plated at a density of 10,000-15,000 cells per well of each 96-well black tissue culture treated microtiter plate, then were grown for 1 hour at 37° C. with 5% CO$_2$/95% air in a humidified incubator to allow cells to attach before compound addition. Compound stocks (100×) were prepared in 96-well V-bottom polypropylene microtiter plates. Five serial (1:2) dilutions were made with anhydrous DMSO at 100× the final concentration used in the assay. The individual wells in compound-containing 384 well plates were diluted 1:10 with complete cell culture medium and the 10× (10 µL) stocks were added to 90 µl of cells in each plate to ensure full mixing of stocks with culture media by using a Biomek FX liquid handler with 96-well head. Doxorubicin was used as the control to monitor the behavior of each cell line. Cells were incubated with the compounds for 3 to 4 days before fluorescence and luminescence reading. Test plates were removed from the incubator and washed once in sterile PBS to remove serum containing calcium esterases. Calcein AM (acetoxymethyl ester) reagent was added and the cells were incubated for 30 min at 37° C. Plates were read for emission by using a fluorescein filter (excitation 485 nm, emission 535 nm). An equal volume (30 µL) of Cell Titer-Glo reagent (Promega Corporation, Inc.) was added and incubated for 10 min at room temperature with gentle agitation to lyse the cells. Each plate was re-read for luminescence to confirm the inhibition observed in the fluorescent Calcium AM assay as a measure of cell viability. The cancer cell cytotoxicity assays were run in triplicate using ≥5 different drug concentrations, and the data were analyzed to establish statistical significance and a valid IC50 value for inhibition of cell growth, based on ≥2 log differences in drug effect.

Example 6

Figure 2:
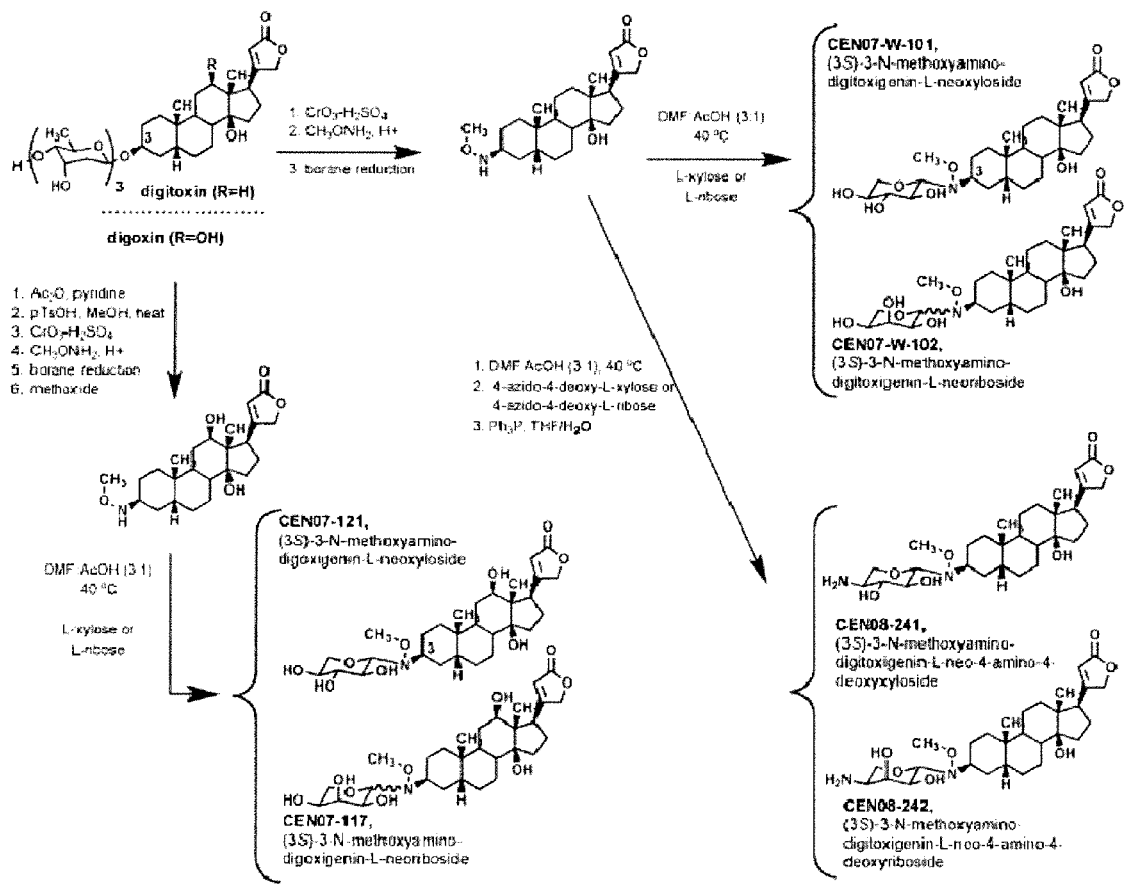
FIG. 2 shows synthesis and structures of neoglycoside analogs made from digitoxin or digoxin.
Figure 3:
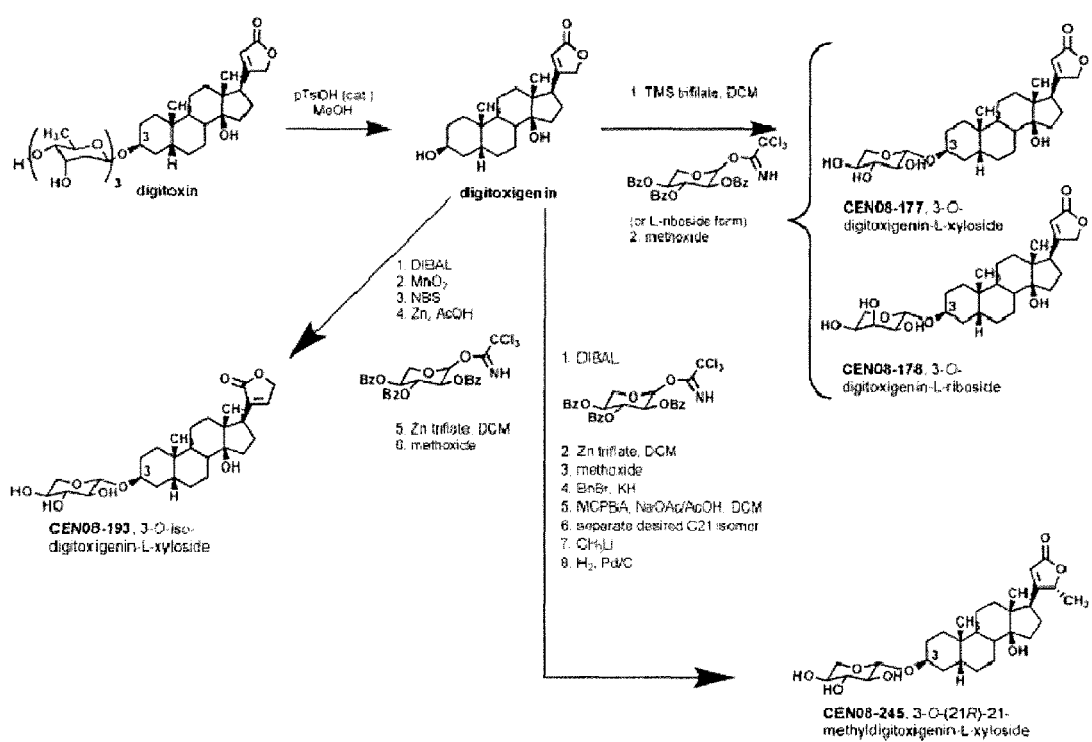
FIG. 3 shows synthesis and structures of O-glycoside analogs made from digitoxin.
Figure 4:
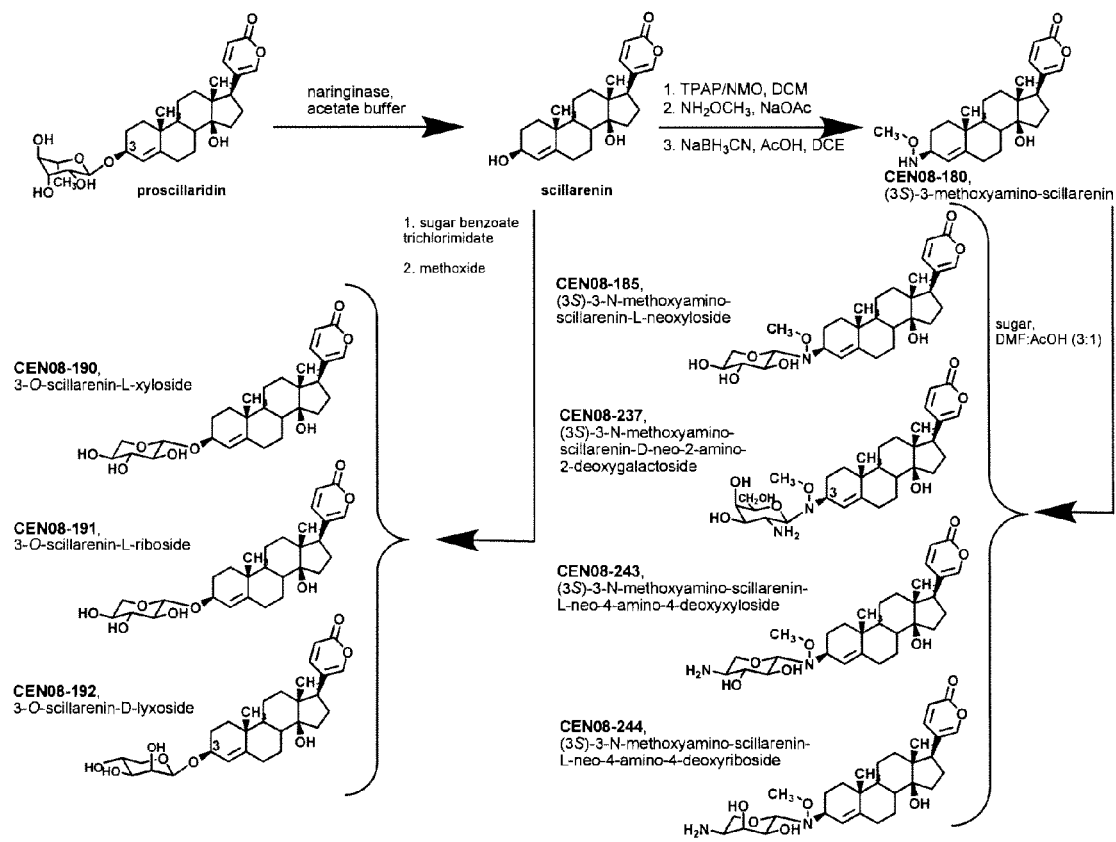
FIG. 4 shows synthesis and structures of neoglycoside and O-glycoside analogs made from proscillaridin.

The cancer cell cytotoxicities (determined substantially according to the method of Example 5) of various compounds of the invention and comparative compounds as determined in four to five different human cancer cell lines are shown in Table 1. The structures of the compounds listed are found in FIGS. 2-4. As shown in Table 1, CEN08-178, CEN08-193, CEN08-243 and CEN08-244 have notably high potency as reflected in IC$_{50}$ values less than 80 nM (and generally below 11 nM) and thus are superior to various comparator compounds.

Example 8

An antitumor assay of CEN08-178, CEN08-193, CEN08-243 and CEN08-244 in the colo205 mouse xenograft model is performed to establish schedule dependency. Inclusion of CEN07-W-101 in the assay allows for comparison of its antitumor efficacy parameters (see above) with those of the compounds of the invention. CEN07-W-101, formulated in

TABLE 1

Cancer Cell Cytotoxicities of Various Inventive and Comparative Compounds

| | Cell Line Number | | | | |
|---|---|---|---|---|---|
| | A549[1] | H1299[1] | NCI-H460[1] | HT29[1] | SKOV3[1] |
| | | | Cell Line Type | | |
| Compound | NSCLC | NSCLC | NSCLC | Colorectal | Ovarian |
| Digitoxin[2] | 280 | | 280 | | 700 |
| (3β)-3-N-methoxy aminodigitoxigenin[2] | 8300 | | 2400 | | 3000 |
| CEN07-W-101 (23S) | 4[5], 9[7], 50[3], 79[2] | 6[5], 17, 170[3] | 8[5], 37[7], 80[2], 150[3] | 9[5], 46[7], 100[3] | 22, 39[5], 39, 51[7], 220[2], 370 |
| CEN07-W-102 (5S) | 3[5], 8[7], 10[4], 17[6], 33[2], 40[3] | 6[5], 9, 20[4,6], 110[3] | 5[5], 10[4], 15[6], 24[7], 53[2], 110[3] | 7[5], 20, 33[7], 120[3] | 25[5], 26[5], 36[7], 40[4], 45[2], 310 |
| CEN07-117 | 340 | 500 | 350 | 440 | 550 |
| CEN07-121 | 150 | 430 | 160 | 230 | 300 |
| CEN08-177 | 20 | 40 | 20 | 70 | 80 |
| CEN08-178 | 20 | 50 | 20 | 70 | 80 |
| CEN08-193 | 4 | 6 | 9 | 11 | 51 |
| CEN08-241 | 20 | 24 | 27 | | 74 |
| CEN08-242 | 50 | 159 | 74 | | 228 |
| CEN08-245 | 1290 | 3700 | 2100 | | 3220 |
| proscillaridin | 2[5], 3[7], 12[6] | 3[5], 4[7], 8[6] | 5[5], 11[7], 12[6] | 7[5], 10[7] | 11[7], 12, 15[6], 45[5] |
| CEN08-190 | 4 | 4 | 6 | 6 | 28 |
| CEN08-191 | 9 | 10 | 17 | 16 | 67 |
| CEN08-192 | 8 | 11 | 16 | 16 | 72 |
| (3β)-3-N-methoxy aminoscillarenin (CEN08-180) | 3 | 8 | 13 | 26 | 34 |
| CEN08-185 | 2 | 5 | 9 | 13 | 15 |
| CEN08-237 | 21 | 20 | 37 | | |
| CEN08-243 | 3 | 7 | 5 | | 5 |
| CEN08-244 | 4 | 10 | 6 | | 6 |

[1]IC$_{50}$ values (nM) were determined at the University of Wisconsin Small Molecule Screening Facility in different sets of assays using the protocol described herein.
[2]Data from Langenhan et al., *Proc Nat Acad Sci USA* 2005, 102(35), 12305-10.
[3]Data determined at same time as CEN07-117 and -121.
[4]Data determined at same time as CEN08-177 and -178.
[5]Data determined at same time as CEN08-193.
[6]Data determined at same time as CEN08-243 and -244.
[7]Data determined at same time as CEN08-180.

Example 7

PK characteristics of CEN08-178, CEN08-193, CEN08-243 and CEN08-244 are evaluated in the nude mouse. Each compound is administered to outbred, female nude mice, formulated in hydroxypropyl-β-cyclodextrin (3-5 mg/ml), by the p.o. route at the MTD (≤30-50 mg/kg) and ~100 μL samples are collected by retro-orbital bleed into EDTA capillaries or vials at 0, 15, 30 and 60 min; >200 μL samples are collected by terminal cardiac puncture into EDTA vials at 2, 4, 8 and 24 hr. Similarly, each compound is administered by the i.v. route at 25% of the MTD (≤8 mg/kg) and ~100 μL samples are collected by retro-orbital bleed into EDTA capillaries or vials at 0, 15, 30 and 60 min; >200 μL samples are collected by terminal cardiac puncture into EDTA vials at 2, 4, 8 and 24 hr. Plasma samples are frozen at −80° C. until analyzed by LC-MS or LC-MS/MS in single assay runs with a standard curve. Concentration-time data are determined and PK parameters are calculated on the basis of a single compartment model for each route of administration.

hydroxypropyl-β-cyclodextrin (3-5 mg/ml), is administered QD×14 by the i.v. route at 10, 5 and 2.5 mg/kg/injection to groups of 8 female nude mice bearing colo205 subcutaneous tumors with a mean tumor burden of 100-150 mg that is within 10% of the overall tumor burden for the entire study. Similar studies are carried out Q12H×2, QD×14 and Q4D×4 by the i.v. route of administration, with the dose (mg/kg/injection) adjusted to achieve the same total dose per group as in the first study and a similar drug exposure per dose based on the PK characteristics. Vehicle only is the control. Animals are monitored for clinical signs daily, and individual body weights and tumor burdens are recorded 2×/wk. Animals in obvious distress or moribund condition, and any animal with an estimated tumor burden >2 g are euthanized. The studies are continued to allow for tumor growth delay. Tumor regressions, tumor free survivors, and T/C values are secondary endpoints. The results are analyzed statistically to allow comparison of antitumor efficacy at the MTD and lower dosages between the different schedules.

The optimal schedule for CEN07-W-101 is chosen on the basis of antitumor potency (lowest effective dose) vs. MTD, tumor progression delay and percentage of complete regressions and remissions and is used as the basis for subsequent antitumor efficacy studies of CEN08-178, CEN08-193, CEN08-243 and CEN08-244 in the colo205 mouse xenograft model, using the i.v. route of administration at the MTD, 0.62×MTD, 0.38×MTD and 0.24×MTD for each drug. CEN07-W-101 at its MTD and vehicle only are controls. The study parameters and endpoints are the same as above.

Example 9

An antitumor assay of CEN08-178, CEN08-193, CEN08-243 and CEN08-244 in the A549 and H23 NSCLC mouse xenograft models is performed. This study is carried out by the optimum schedule established in Example 8 using SCID female mice bearing A549 NSCLC subcutaneous xenografts and female nude mice bearing H23 NSCLC subcutaneous xenografts. The study parameters and endpoints are the same as in Example 7. The compounds of the invention are expected to show similar antitumor properties as those established in Example 8 but with a lower effective dose due to the greater potency of these compounds Example 10

The MTD of the compounds of the invention is determined in transgenic mice whose Na,K-ATPase α1β1 isoform has been rendered sensitive to cardiac glycosides, including the compounds of the invention, by site specific mutation of the gene (Dostanic-Larson, et al., *Am J Physiol Regul Integr Comp Physiol*. 290:R524-8, 2006; Dostanic, et al., *J Biol Chem*. 279:54053-61, 2004) to overcome the high resistance of this enzyme in normal mice. Groups of 5 to 8 mice carrying the sensitive isoform are injected retroorbitally with solutions of CEN08-178, CEN08-193, CEN08-243 and CEN08-244 (formulated in 15% hydroxypropyl-β-cyclodextrin:water at 1 mg/ml), at concentrations of 0.5, 1, 3, 6 mg/kg plus the following two drugs as comparators, CEN07-W-102 at concentrations of 0.5, 1, 3, 6 mg/kg and digitoxin as concentrations of 0.25, 0.5, 1 and 3 mg/kg. Normal mice of similar genetic parentage but with the resistant Na,K-ATPase α1β1 isoform are injected with the same drugs but at higher concentrations consistent with the known MTD values in such mice. One group of Na,K-ATPase α1β1 isoform sensitive and one group of normal mice with the resistant α1β1 isoform injected with vehicle only are used as controls. The observed parameters of toxicity include staggering, limb extension, tremor or convulsion, labored breathing and loss of righting reflex, as well as animal weight, are determined daily for 7 days. The MTD is the drug dosage that causes observed signs of toxicity during the first 24 hr without resulting in animal death.

BIBLIOGRAPHY

Haux. *Med Hypotheses* 53:543-8, 1999.
Johansson, et al. *Anticancer Drugs* 12:475-83, 2001.
Mijatovic, et al. *Biochim Biophys Acta* 1776:32-57, 2007.
Repke, et al. Approach to the chemotopography of the digitalis recognition matrix in Na+/K+-transporting ATPase as a step in the rational design of new inotropic steroids. Elsevier Science New York City. (1993), 135-202.
Mudge, et al. *Circ Res* 43:847-54, 1978.
Repke. *Drug Discovery Today* 2:110-16, 1997.
Schneider, et al. *Curr Org Chem* 8:1381-403, 2004.
Langenhan, et al. *Proc Natl Acad Sci USA* 102:12305-10, 2005.
Gardiner, et al. Modulators of hypoxia inducible factor-1 and related uses. BTG plc, US. (2009), 1-67.
Mijatovic, et al. *Drug Dev. Res.* 68:164-73, 2007.
Wiesner, et al. *Pure Applied Chemistry* 58:799-810, 1986.
Pastclin, et al. *Life Sci* 32:1905-9, 1983.
Caldwell, et al. *J Pharmacol Exp Ther* 197:19-26, 1976.
Zhang, et al. *Proc Natl Acad Sci USA* 105:19579-86, 2008.
Khodadoust, et al. *Treatment of refractory cancers using Na+/K+-ATPase inhibitors*. Bionaut Pharmaceuticals, Inc., USA. (2008), 1-55.
Mijatovic, et al. *Cancer Lett* 2009.
Prassas, et al. *Nat Rev Drug Discov* 7:926-35, 2008.
Aperia. Journal of Internal Medicine 261:44-52, 2007.
Chou. *Pharmacol Rev* 58:621-81, 2006.
Dostanic-Larson, et al. *Am J Physiol Regul Integr Comp Physiol* 290:R524-8, 2006.
Dostanic, et al. *J Biol Chem* 279:54053-61, 2004.

What is claimed is:

1. A compound of formula I:

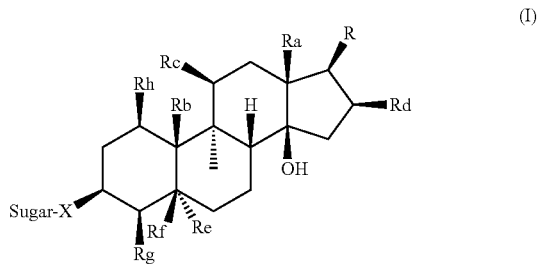

or a pharmaceutically acceptable ester, conjugate, hydrate, solvate or salt thereof, wherein:

R is selected from the group consisting of

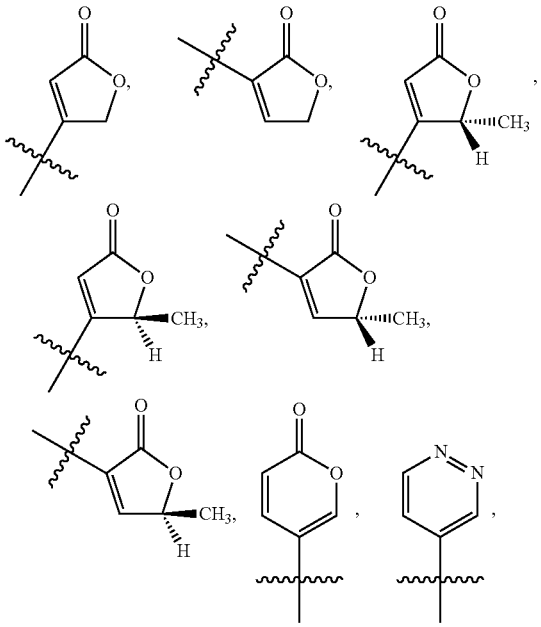

-continued

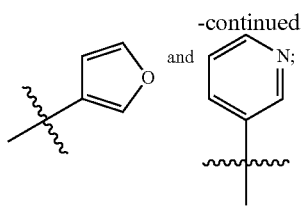

$R_a$ is $CH_3$;
$R_b$ is $CH_3$, $CH_2OH$, or CHO;
$R_c$ is H, OH, or $CH_3COO$;
$R_d$ is H or OH;
$R_e$ is H or absent when $R_f$ is H, OH or a C=C exists between the atoms joined to $R_e$, $R_f$ and $R_g$;
$R_f$ is H, OH, or absent when $R_e$ is H or a C=C exists between the atoms joined to $R_e$, $R_f$ and $R_g$;
$R_g$ is H or when a C=C exists between the atoms joined to $R_e$, $R_f$ and $R_g$, $R_g$ is no group;
$R_h$ is H or OH;
X is O;
R' is an alkyl or aryl group; and
Sugar is selected from the group consisting of

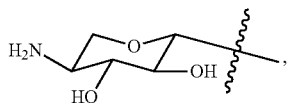

-continued

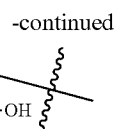

and their epimers and conformers.

2. A pharmaceutical composition comprising a compound of claim 1 and at least one pharmaceutically acceptable excipient.

3. The pharmaceutical composition of claim 2 wherein the at least one pharmaceutically acceptable excipient is a cyclodextrin.

4. A method of treating cancer in a subject in need thereof, the method comprising administering to the subject a therapeutically effective amount of a pharmaceutical composition of claim 2.

5. A method for treating hyperproliferative disease in a subject in need thereof, the method comprising administering to the subject a therapeutically effective amount of a compound of claim 1.

6. The method of claim 4 wherein the cancer is selected from colorectal, non-small cell, lung, ovarian, breast, colon, CNS, liver, lung, and kidney cancers.

* * * * *